(12) United States Patent
Pinczuk et al.

(10) Patent No.: US 11,819,335 B2
(45) Date of Patent: Nov. 21, 2023

(54) SYSTEMS AND METHODS FOR ADJUSTING USER POSITION USING MULTI-COMPARTMENT BLADDERS

(71) Applicant: ResMed Sensor Technologies Limited, Dublin (IE)

(72) Inventors: Michael Pinczuk, Sydney (AU); Kieran Grennan, Dublin (IE); Ian Andrew Law, Sydney (AU)

(73) Assignee: ResMed Sensor Technologies Limited, Dublin (IE)

( * ) Notice: Subject to any disclaimer, the term of this patent is extended or adjusted under 35 U.S.C. 154(b) by 0 days.

(21) Appl. No.: 17/780,967

(22) PCT Filed: Nov. 27, 2020

(86) PCT No.: PCT/IB2020/061244
§ 371 (c)(1),
(2) Date: May 27, 2022

(87) PCT Pub. No.: WO2021/105957
PCT Pub. Date: Jun. 3, 2021

(65) Prior Publication Data
US 2023/0000428 A1   Jan. 5, 2023

Related U.S. Application Data

(60) Provisional application No. 62/942,097, filed on Nov. 30, 2019.

(51) Int. Cl.
*A61B 5/00* (2006.01)
*A61M 16/00* (2006.01)
(Continued)

(52) U.S. Cl.
CPC .............. *A61B 5/4806* (2013.01); *A61F 5/56* (2013.01); *A61M 16/024* (2017.08); *A47G 9/10* (2013.01);
(Continued)

(58) Field of Classification Search
CPC ... A61B 5/4806; A61B 5/4809; A61B 5/4812; A61B 5/4815; A61B 5/4818; A61B 5/08;
(Continued)

(56) References Cited

U.S. PATENT DOCUMENTS

| 9,681,838 B2 | 6/2017 | Halperin | |
|---|---|---|---|
| 2007/0061976 A1 * | 3/2007 | Bazargani | ............ A47G 9/1027 5/644 |

(Continued)

FOREIGN PATENT DOCUMENTS

| JP | 2006-061201 | | 3/2006 | |
|---|---|---|---|---|
| KR | 20080112613 A | * | 6/2007 | ........... A47G 9/1027 |

(Continued)

OTHER PUBLICATIONS

English Machine Translation of KR-101643545-B1 provided by PE2E (Year: 2016).*

(Continued)

*Primary Examiner* — Joseph D. Boecker
*Assistant Examiner* — Brian T Khong
(74) *Attorney, Agent, or Firm* — Nixon Peabody LLP

(57) ABSTRACT

A method includes receiving data associated with a sleep session of a user. The method also includes determining that the user is experiencing or has experienced an event based at least in part on the data. The method also includes causing pressurized air to be directed from a respiratory device to a multi-compartment bladder in response to determining that (Continued)

the user is experiencing or has experienced the event to aid in modifying a position of a head of the user.

27 Claims, 14 Drawing Sheets

(51) Int. Cl.
*A61F 5/56* (2006.01)
*A47G 9/10* (2006.01)

(52) U.S. Cl.
CPC . *A61M 2016/0027* (2013.01); *A61M 2230/63* (2013.01)

(58) Field of Classification Search
CPC ..... A61B 5/087; A61B 5/0816; A61B 5/6887; A61B 5/1116; A61F 5/56; A47G 9/1027
See application file for complete search history.

(56) References Cited

U.S. PATENT DOCUMENTS

| | | |
|---|---|---|
| 2011/0295083 A1 | 12/2011 | Doelling |
| 2016/0089261 A1* | 3/2016 | Quinn ................... A61M 16/06 128/848 |

FOREIGN PATENT DOCUMENTS

| | | | | |
|---|---|---|---|---|
| KR | 101643545 B1 | * | 4/2016 | ........... A47G 9/1027 |
| KR | 101762116 B1 | * | 3/2017 | ........... A47G 9/1027 |
| KR | 102023362 B1 | * | 4/2019 | ........... A47G 9/1027 |
| WO | 2007/052108 | | 5/2007 | |
| WO | 2013/177621 | | 12/2013 | |
| WO | WO-2016054949 A1 | * | 4/2016 | ........... A47G 9/1027 |

OTHER PUBLICATIONS

English Machine Translation of KR-20080112613-A provided by PE2E (Year: 2007).*
English Machine Translation of KR-101762116-B1 provided by PE2E (Year: 2017).*
English Machine Translation of WO-2016054949-A1 provided by PE2E (Year: 2016).*
English Machine Translation of KR-102023362-B1 provided by PE2E (Year: 2019).*
International Search Report and Written Opinion in International Application No. PCT/IB2020/061244, dated Mar. 1, 2021 (16 pages).

* cited by examiner

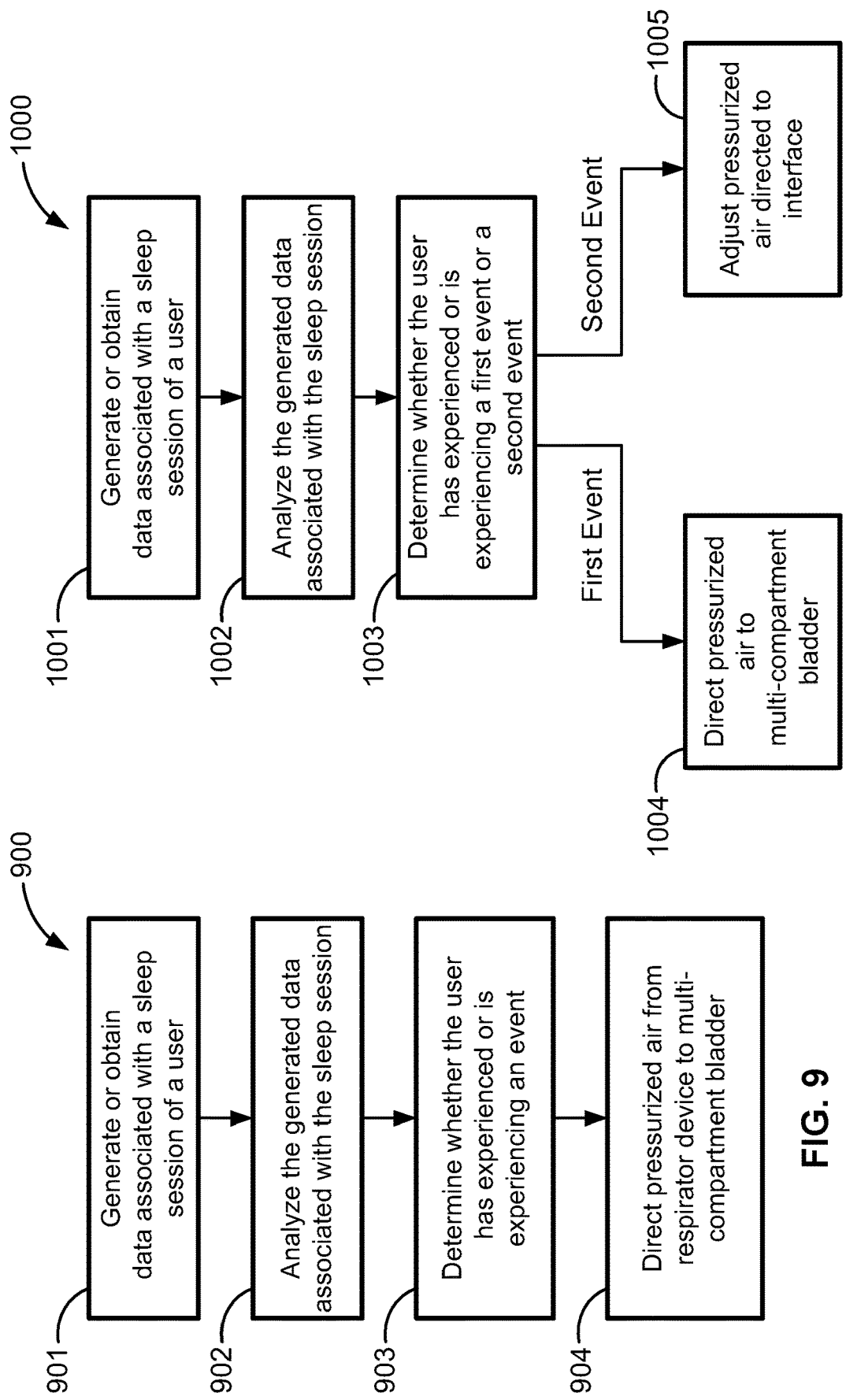

SYSTEMS AND METHODS FOR ADJUSTING USER POSITION USING MULTI-COMPARTMENT BLADDERS

CROSS-REFERENCE TO RELATED APPLICATIONS

This application is a U.S. National Stage of International Application No. PCT/IB2020/061244, filed Nov. 27, 2020, which claims the benefit of, and priority to, U.S. Provisional Patent Application No. 62/942,097, filed Nov. 30, 2019, each of which is hereby incorporated by reference herein in its entirety.

TECHNICAL FIELD

The present disclosure relates generally to systems and methods for treating respiratory events during a sleep session, and more particularly, to systems and methods for adjusting a user position during a sleep session using a multi-compartment bladder.

BACKGROUND

Many individuals suffer from sleep-related respiratory disorders that cause one or more events during a sleep session, such as, for example, snoring, apneas, hypopneas, restless leg, a sleeping disorder, choking, an increased heart rate, labored breathing, asthma attacks, epileptic episodes, seizures, etc., or any combination thereof. While the occurrence of these events can be eliminated or substantially reduced using a respirator device, many of these events can be treated by adjusting a position of the individual during a sleep session. The present disclosure is directed to solving these and other problems.

SUMMARY

According to some implementations of the present disclosure, a method includes receiving data associated with a sleep session of a user. The method also includes determining that the user is experiencing or has experienced an event based at least in part on the data. The method also includes causing pressurized air to be directed from a respiratory device to a multi-compartment bladder in response to determining that the user is experiencing or has experienced the event to aid in modifying a position of a head of the user.

According to some implementations of the present disclosure, a system includes a respiratory device, a sensor, a multi-compartment bladder, a memory, and a control system. The respiratory device is configured to supply, by way of a user interface coupled to the respiratory device via a conduit, pressurized air to an airway of a user during a sleep session. The sensor is configured to generate data associated with the sleep session. The multi-compartment bladder is coupled to the respiratory device and is configured to be positioned adjacent to a user during the sleep session. The memory stores machine-readable instructions. The control system includes one or more processors configured to execute the machine-readable instructions to determine, based at least in part on data, that the user is experiencing or has experienced an event. The control system is further configured to cause at least a portion of the supplied pressurized air to be directed to the multi-compartment bladder responsive to determining that the user is experiencing or has experienced the event.

According to some implementations of the present disclosure, a system includes a respiratory device, a sensor, a multi-compartment bladder, a valve, a memory, and a control system. The respiratory device is configured to supply, by way of a user interface coupled to the respiratory device via a first tube, pressurized air to an airway of a user during a sleep session. The sensor is configured to generate data associated with the sleep session. The multi-compartment bladder is coupled to the respiratory device via a second tube. The valve is in fluid communication with the respiratory device, the first tube, and the second tube. The memory stores machine-readable instructions. The control system includes one or more processors configured to execute the machine-readable instructions to determine that the user is experiencing or has experienced an event based at least in part on the data. The control system is further configured to responsive to determining that the user is experiencing or has experienced the event, cause the valve to direct at least a portion of the supplied pressurized air to the multi-compartment bladder via the second tube to aid in causing a head of the user to move.

According to some implementations of the present disclosure, a system includes a respiratory device, a sensor, a multi-compartment bladder, a memory, and a control system. The respiratory device is configured to supply, by way of a user interface coupled to the respiratory device via a conduit, pressurized air to an airway of the user during a sleep session. The sensor is configured to generate data associated with the sleep session of the user. The multi-compartment bladder is coupled to the respiratory device and being configured to be positioned adjacent to a user during the sleep session. The memory stores machine-readable instructions. The control system includes one or more processors configured to execute the machine-readable instructions to: determine, based at least in part on the data, that the user is experiencing or has experienced a first event or a second event. The control system is further configured to, responsive to determining that the user is experiencing or has experienced the first event, cause (i) a first portion of the supplied pressurized air from the respiratory device to be directed to the multi-compartment bladder to aid in causing the user to move and (ii) a second portion of the supplied pressurized air from respiratory device to be directed to the user interface. The control system is further configured to, responsive to determining that the user is experiencing or has experienced the second event, cause the supplied pressurized air from the respiratory device to be directed to the user interface.

According to some implementations of the present disclosure, a system includes a respiratory device, a sensor, a valve, a user interface, a multi-compartment bladder, a memory, and a control system. The respiratory device is configured to supply pressurized air at a plurality of pressures. The sensor is configured to generate data associated with a sleep session of a user of the respiratory device. The valve has an inlet, a first outlet, and a second outlet. The value is configured to receive, via the inlet, the supplied pressurized air and direct the supplied pressurized air to the first outlet, the second outlet, or both. The user interface is coupled to the respiratory device via the first outlet of the valve. The multi-compartment bladder is coupled to the respiratory device via the second outlet of the valve. The memory stores machine-readable instructions. The control system includes one or more processors configured to execute the machine-readable instructions to cause the respiratory device to supply the pressurized air at a first pressure. The control system is further configured to cause the valve to direct the supplied pressurized air to the first outlet and not the second outlet. The control system is further configured to analyze the generated data associated with the sleep session of the user. The control system is further configured to determine, based at least in part on the analysis, that the user is experiencing or has experienced a first event. The control system is further configured to, responsive to the determination that the user is experiencing or has experienced the first event, (i) cause the respiratory device to supply the pressurized air at a second pressure that is greater than the first pressure and (ii) cause the valve to direct the supplied pressurized air to the second outlet and not the first outlet to inflate at least a portion of the multi-compartment bladder. The control system is further configured to determine, based at least in part on the analysis, that the user is experiencing or has experienced a second event, the second event occurring subsequent to the first event. The control system is further configured to, responsive to the determination that the user is experiencing or has experienced the second event, (i) cause the respiratory device to supply the pressurized air at a third pressure that is greater than the first pressure and (ii) cause the valve to direct supplied pressurized air to the first outlet and not the second outlet.

According to some implementations of the present disclosure, a system includes a respiratory device, a sensor, a multi-compartment bladder, one or more memory devices, and a control system. The respiratory device is configured to supply, by way of a user interface coupled to the respirator device via a conduit, pressurized air to an airway of a user during a sleep session. The sensor is configured to generate data associated with the sleep session. The multi-compartment bladder is coupled to the respiratory device. The one or more memory devices store machine-readable instructions. The control system includes one or more processors configured to execute the machine-readable instructions to determine, based at least in part on the generated data, that the user is experiencing or has experienced an event. The control system is further configured to responsive to the determination that the user is experiencing or has experienced the event, cause at least a portion of the supplied pressurized air to be temporarily diverted from the interface and directed to the multi-compartment bladder to aid in inflating at least a portion of the multi-compartment bladder.

According to some implementations of the present disclosure, a system includes a valve, a multi-compartment bladder, one or more memory devices, and a control system. The valve has an inlet, a first outlet, and a second outlet, the inlet of the valve being configured to be coupled to a respiratory device and receive pressurized air therefrom. The multi-compartment bladder is coupled to the second outlet of the valve. The one or more memory devices store machine-readable instructions. The control system includes one or more processors configured to execute the machine-readable instructions to cause the valve to direct the received pressurized air to the first outlet of the valve. The control system is further configured to responsive to a determination that the user is experiencing or has experienced an event, cause the valve to direct the supplied pressurized air to the second outlet of the valve.

The above summary is not intended to represent each embodiment or every aspect of the present invention. Additional features and benefits of the present invention are apparent from the detailed description and figures set forth below.

BRIEF DESCRIPTION OF THE DRAWINGS

FIG. 9 is a process flow diagram for a method of directing at least a portion of the supplied pressurized air from a respirator device to a multi-compartment bladder, according to some implementations of the present disclosure;

FIG. 10 is a process flow diagram for a method of directing a portion of the supplied pressurized air from a respirator device to a multi-compartment bladder responsive to a first event and adjusting the supplied pressurized air directed to an interface responsive to a second event, according to some implementations of the present disclosure;

Figure 1:
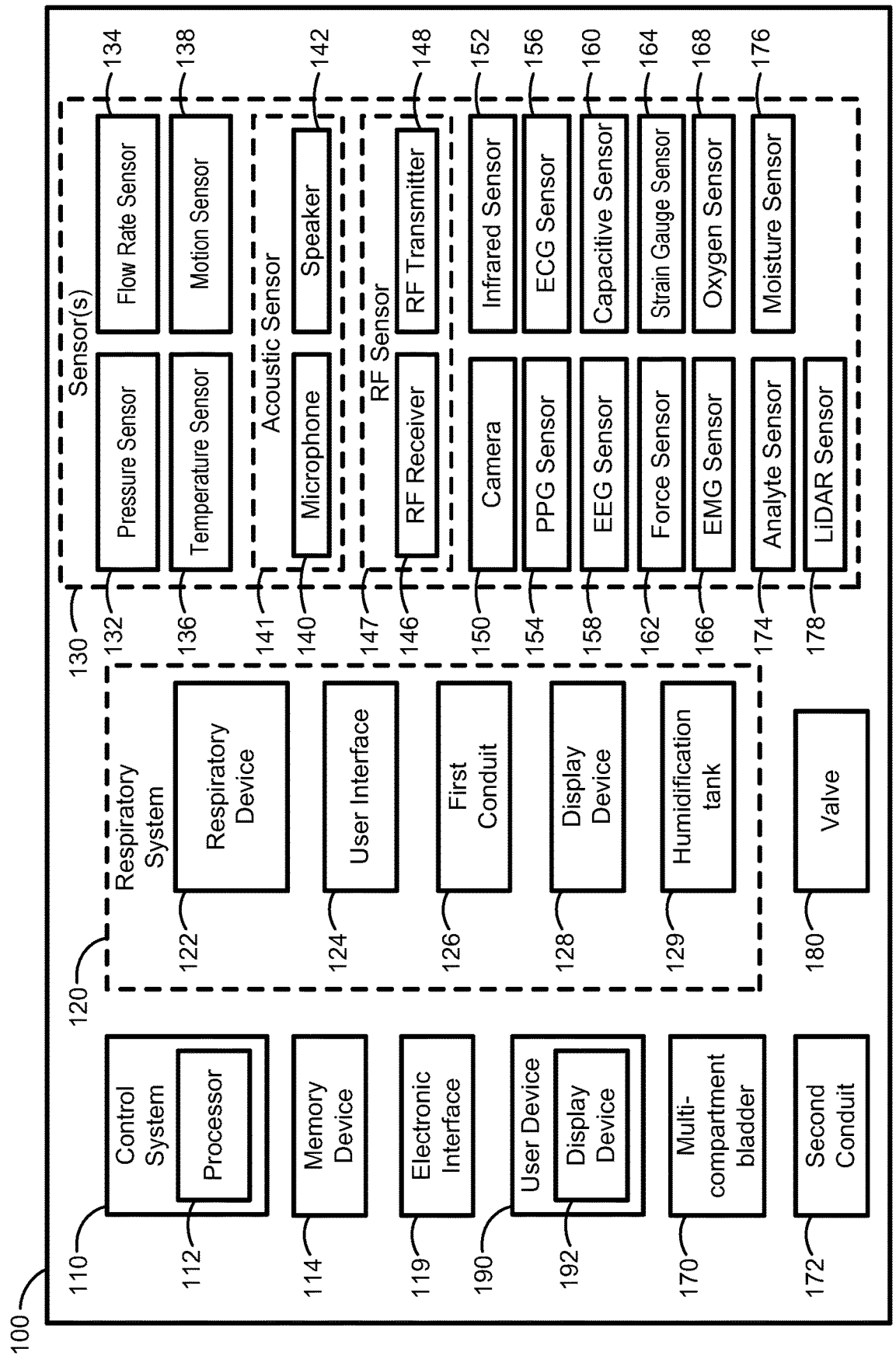
FIG. 1 is a functional block diagram of a system for adjusting a user position during a sleep session, according to some implementations of the present disclosure.

While the disclosure is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Many individuals suffer from sleep-related and/or respiratory disorders. Examples of sleep-related and/or respiratory disorders include Periodic Limb Movement Disorder (PLMD), Restless Leg Syndrome (RLS), Sleep-Disordered Breathing (SDB), Obstructive Sleep Apnea (OSA), apneas, Cheyne-Stokes Respiration (CSR), respiratory insufficiency, Obesity Hyperventilation Syndrome (OHS), Chronic Obstructive Pulmonary Disease (COPD), Neuromuscular Disease (NMD), and chest wall disorders.

Obstructive Sleep Apnea (OSA) is a form of Sleep Disordered Breathing (SDB), and is characterized by events including occlusion or obstruction of the upper air passage during sleep resulting from a combination of an abnormally small upper airway and the normal loss of muscle tone in the region of the tongue, soft palate and posterior oropharyngeal wall. More generally, an apnea generally refers to the cessation of breathing caused by blockage of the air (Obstructive Sleep Apnea) or the stopping of the breathing function (often referred to as central apnea). Typically, the individual will stop breathing for between about 15 seconds and about 30 seconds during an obstructive sleep apnea event.

Other types of apneas include hypopnea, hyperpnea, and hypercapnia. Hypopnea is generally characterized by slow or shallow breathing caused by a narrowed airway, as opposed to a blocked airway. Hyperpnea is generally characterized by an increase depth and/or rate of breathing. Hypercapnia is generally characterized by elevated or excessive carbon dioxide in the bloodstream, typically caused by inadequate respiration.

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterized by repetitive de-oxygenation and re-oxygenation of the arterial blood.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung.

Neuromuscular Disease (NMD) encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

These and other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping.

The Apnea-Hypopnea Index (AHI) is an index used to indicate the severity of sleep apnea during a sleep session. The AHI is calculated by dividing the number of apnea and/or hypopnea events experienced by the user during the sleep session by the total number of hours of sleep in the sleep session. The event can be, for example, a pause in breathing that lasts for at least 10 seconds. An AHI that is less than 5 is considered normal. An AHI that is greater than or equal to 5, but less than 15 is considered indicative of mild sleep apnea. An AHI that is greater than or equal to 15, but less than 30 is considered indicative of moderate sleep apnea. An AHI that is greater than or equal to 30 is considered indicative of severe sleep apnea. In children, an AHI that is greater than 1 is considered abnormal. Sleep apnea can be considered "controlled" when the AHI is normal, or when the AHI is normal or mild. The AHI can also be used in combination with oxygen desaturation levels to indicate the severity of Obstructive Sleep Apnea.

Referring to FIG. 1, a system 100 according to some implementations of the present disclosure is illustrated. The system includes a control system 110, a memory device 114, an electronic interface 119, one or more sensors 130, a multi-compartment bladder 170, a valve 180, and one or more user devices 190. In some implementations, the system 100 further includes a respiratory therapy system 120.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is shown in FIG. 1, the control system 110 can include any suitable number of processors (e.g., one processor, two processors, five processors, ten processors, etc.) that can be in a single housing, or located remotely from each other. The control system 110 can be coupled to and/or positioned within, for example, a housing of the user device 190, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of the respiratory device 122, within a housing of the user device 190, within a housing of one or more of the sensors 130, or any combination thereof. Like the control system 110, the memory device 114 can be centralized (within one such housing) or decentralized (within two or more of such housings, which are physically distinct).

In some implementations, the memory device 114 (FIG. 1) stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a family history of insomnia or sleep apnea, an employment status of the user, an educational status of the user, a socioeconomic status of the user, or any combination thereof. The medical information can include, for example, information indicative of one or more medical conditions associated with the user, medication usage by the user, or both. The medical information data can further include a multiple sleep latency test (MSLT) result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

The electronic interface 119 is configured to receive data (e.g., physiological data and/or audio data) from the one or more sensors 130 such that the data can be stored in the memory device 114 and/or analyzed by the processor 112 of the control system 110. The electronic interface 119 can communicate with the one or more sensors 130 using a wired connection or a wireless connection (e.g., using an RF communication protocol, a WiFi communication protocol, a Bluetooth communication protocol, over a cellular network, etc.). The electronic interface 119 can include an antenna, a receiver (e.g., an RF receiver), a transmitter (e.g., an RF transmitter), a transceiver, or any combination thereof. The electronic interface 119 can also include one more processors and/or one more memory devices that are the same as, or similar to, the processor 112 and the memory device 114 described herein. In some implementations, the electronic interface 119 is coupled to or integrated in the user device 190. In other implementations, the electronic interface 119 is coupled to or integrated (e.g., in a housing) with the control system 110 and/or the memory device 114.

As noted above, in some implementations, the system 100 can also include a respiratory system 120 (also referred to as a respiratory therapy system). The respiratory system 120 can include a respiratory pressure therapy device 122 (referred to herein as respiratory device 122), a user interface 124, a conduit 126 (also referred to as a tube or an air circuit), a display device 128, a humidification tank 129, or any combination thereof. In some implementations, the control system 110, the memory device 114, the display device 128, one or more of the sensors 130, and the humidification tank 129 are part of the respiratory device 122. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory system 120 is generally used to treat individuals suffering from one or more sleep-related respiratory disorders (e.g., obstructive sleep apnea, central sleep apnea, or mixed sleep apnea).

The respiratory device 122 is generally used to generate pressurized air that is delivered to a user (e.g., using one or more motors that drive one or more compressors). In some implementations, the respiratory device 122 generates continuous constant air pressure that is delivered to the user. In other implementations, the respiratory device 122 generates two or more predetermined pressures (e.g., a first predetermined air pressure and a second predetermined air pressure). In still other implementations, the respiratory device 122 is configured to generate a variety of different air pressures within a predetermined range. For example, the respiratory device 122 can deliver at least about 6 cm $H_2O$, at least about 10 cm $H_2O$, at least about 20 cm $H_2O$, between about 6 cm $H_2O$ and about 10 cm $H_2O$, between about 7 cm $H_2O$ and about 12 cm $H_2O$, etc. The respiratory device 122 can also deliver pressurized air at a predetermined flow rate between, for example, about −20 L/min and about 150 L/min, while maintaining a positive pressure (relative to the ambient pressure).

The user interface 124 engages a portion of the user's face and delivers pressurized air from the respiratory device 122 to the user's airway to aid in preventing the airway from narrowing and/or collapsing during sleep. This may also increase the user's oxygen intake during sleep. Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 cm $H_2O$.

Figure 2:
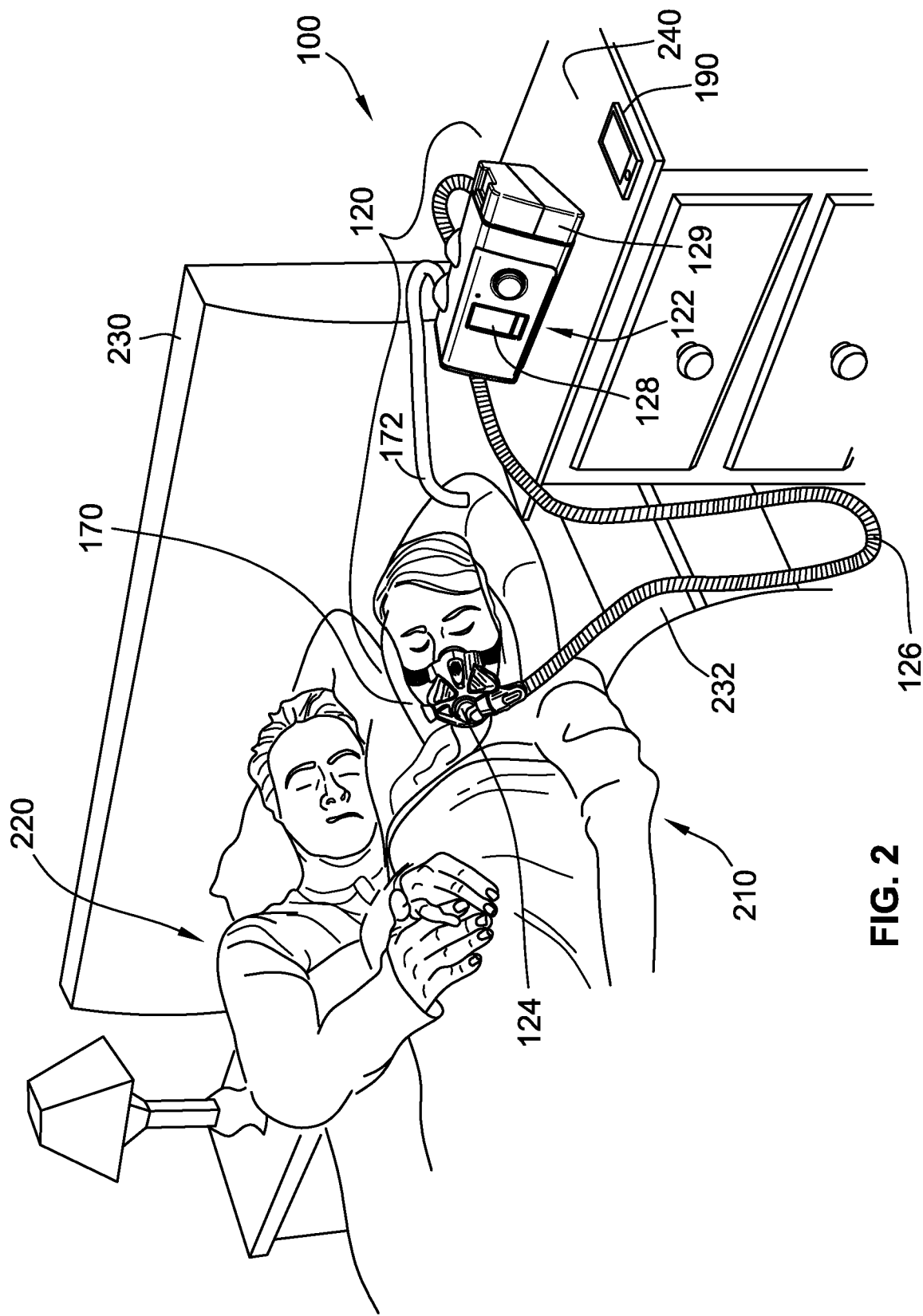
FIG. 2 is a perspective view of at least a portion of the system of FIG. 1, a user, and a bed partner, according to some implementations of the present disclosure.

As shown in FIG. 2, in some implementations, the user interface 124 is a facial mask that covers the nose and mouth of the user. Alternatively, the user interface 124 can be a nasal mask that provides air to the nose of the user or a nasal pillow mask that delivers air directly to the nostrils of the user. The user interface 124 can include a plurality of straps (e.g., including hook and loop fasteners) for positioning and/or stabilizing the interface on a portion of the user (e.g., the face) and a conformal cushion (e.g., silicone, plastic, foam, etc.) that aids in providing an air-tight seal between the user interface 124 and the user. The user interface 124 can also include one or more vents for permitting the escape of carbon dioxide and other gases exhaled by the user 210. In other implementations, the user interface 124 comprises a mouthpiece (e.g., a night guard mouthpiece molded to conform to the user's teeth, a mandibular repositioning device, etc.).

The conduit 126 (also referred to as an air circuit or tube) allows the flow of air between two components of a respiratory system 120, such as the respiratory device 122 and the user interface 124. In some implementations, there can be separate limbs of the conduit for inhalation and exhalation. In other implementations, a single limb conduit is used for both inhalation and exhalation.

One or more of the respiratory device 122, the user interface 124, the conduit 126, the display device 128, and the humidification tank 129 can contain one or more sensors (e.g., a pressure sensor, a flow rate sensor, or more generally any of the other sensors 130 described herein). These one or more sensors can be use, for example, to measure the air pressure and/or flow rate of pressurized air supplied by the respiratory device 122.

The display device 128 is generally used to display image(s) including still images, video images, or both and/or information regarding the respiratory device 122. For example, the display device 128 can provide information regarding the status of the respiratory device 122 (e.g., whether the respiratory device 122 is on/off, the pressure of the air being delivered by the respiratory device 122, the temperature of the air being delivered by the respiratory device 122, etc.) and/or other information (e.g., a sleep score, the current date/time, personal information for the user 210, etc.). In some implementations, the display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory device 122.

The humidification tank 129 is coupled to or integrated in the respiratory device 122 and includes a reservoir of water that can be used to humidify the pressurized air delivered from the respiratory device 122. The respiratory device 122 can include a heater to heat the water in the humidification tank 129 in order to humidify the pressurized air provided to the user. Additionally, in some implementations, the conduit 126 can also include a heating element (e.g., coupled to and/or imbedded in the conduit 126) that heats the pressurized air delivered to the user.

The respiratory system 120 can be used, for example, as a ventilator or as a positive airway pressure (PAP) system, such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Forcing pressurized air into the user's throat/airway using the respirator system can cause one or more adverse side effects, such as, for example, dryness in the nose and/or mouth, a sore throat, etc. The pressurized air can also force air into the stomach, causing general discomfort, bloating, and/or gas. As another example, the pressurized air can cause a vacuum effect leading to stomach reflux. If the engagement between the user and the interface does not form a substantially air-tight seal, pressurized air can leak from the interface causing undesirable noise that may wake the user and/or their bed partner, dryness or irritation of the eyes and/or skin, and/or lower the volume of air being delivered to the user (e.g., which may necessitate an increase in pressure), thereby impeding the proper delivery of therapy. Air leakage from the interface can occur, for example, if the user is laying on their side as opposed to laying on their back while sleeping.

In at least some cases, changing the physical position of the user or a portion of the user during the sleep session (e.g., tilting the head of the user forward to open the airway) can prevent and/or reduce the occurrence of one or more of the events described herein and/or reduce the severity of these events, for example, in instances of positional sleep apnea where apneic episodes are associated with the user's sleeping position, and modifying the sleeping position of the user can aid in reducing or preventing such events. For example, changing the physical position of the user (e.g., rotating the user onto their back) can aid in reducing or preventing air leakage from the interface. Adjustment(s) to the physical position of the user during the sleep session can be used in conjunction with the respirator system as a further measure to reduce, prevent, and/or address the occurrence of an event, or independently of the respirator system. Even if adjusting the position of the user does not by itself reduce, eliminate, and/or address an event, the adjusted position can reduce the required pressure that needs to be delivered by the respirator system to the airway of the user for effective therapy (e.g., 10% less pressure, 30% less pressure, 50% less pressure, 75% less pressure, etc.).

Referring to FIG. 2, a portion of the system 100 (FIG. 1), according to some implementations, is illustrated. A user 210 of the respiratory system 120 and a bed partner 220 are located in a bed 230 and are laying on a mattress 232. The user interface 124 (e.g., a full facial mask) can be worn by the user 210 during a sleep session. The user interface 124 is fluidly coupled and/or connected to the respiratory device 122 via the conduit 126. In turn, the respiratory device 122 delivers pressurized air to the user 210 via the conduit 126 and the user interface 124 to increase the air pressure in the throat of the user 210 to aid in preventing the airway from closing and/or narrowing during sleep. The respiratory device 122 can be positioned on a nightstand 240 that is directly adjacent to the bed 230 as shown in FIG. 2, or more generally, on any surface or structure that is generally adjacent to the bed 230 and/or the user 210.

Referring to back to FIG. 1, the one or more sensors 130 of the system 100 include a pressure sensor 132, a flow rate sensor 134, temperature sensor 136, a motion sensor 138, a microphone 140, a speaker 142, a radio-frequency (RF) receiver 146, a RF transmitter 148, a camera 150, an infrared sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, a LiDAR sensor 178, or any combination thereof. Generally, each of the one or sensors 130 are configured to output sensor data that is received and stored in the memory device 114 or one or more other memory devices.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the infrared sensor 152, the photoplethysmogram (PPG) sensor 154, the electrocardiogram (ECG) sensor 156, the electroencephalography (EEG) sensor 158, the capacitive sensor 160, the force sensor 162, the strain gauge sensor 164, the electromyography (EMG) sensor 166, the oxygen sensor 168, the analyte sensor 174, the moisture sensor 176, and the LiDAR sensor 178, more generally, the one or more sensors 130 can include any combination and any number of each of the sensors described and/or shown herein.

The one or more sensors 130 can be used to generate, for example, physiological data, audio data, or both. Physiological data generated by one or more of the sensors 130 can be used by the control system 110 to determine a sleep-wake signal associated with a user during a sleep session and one or more sleep-related parameters. The sleep-wake signal can be indicative of one or more sleep states, including wakefulness, relaxed wakefulness, micro-awakenings, a rapid eye movement (REM) stage, a first non-REM stage (often referred to as "N1"), a second non-REM stage (often referred to as "N2"), a third non-REM stage (often referred to as "N3"), or any combination thereof. The sleep-wake signal can also be timestamped to indicate a time that the user enters the bed, a time that the user exits the bed, a time that the user attempts to fall asleep, etc. The sleep-wake signal can be measured by the sensor(s) 130 during the sleep session at a predetermined sampling rate, such as, for example, one sample per second, one sample per 30 seconds, one sample per minute, etc. Examples of the one or more sleep-related parameters that can be determined for the user during the sleep session based on the sleep-wake signal include a total time in bed, a total sleep time, a sleep onset latency, a wake-after-sleep-onset parameter, a sleep efficiency, a fragmentation index, or any combination thereof.

Physiological data and/or audio data generated by the one or more sensors 130 can also be used to determine a respiration signal associated with a user during a sleep session. The respiration signal is generally indicative of respiration or breathing of the user during the sleep session. The respiration signal can be indicative of, for example, a respiration rate, a respiration rate variability, an inspiration amplitude, an expiration amplitude, an inspiration-expiration ratio, a number of events per hour, a pattern of events, pressure settings of the respiratory device 122, or any combination thereof. The event(s) can include snoring, apneas, central apneas, obstructive apneas, mixed apneas, hypopneas, a mask leak (e.g., from the user interface 124), a restless leg, a sleeping disorder, choking, an increased heart rate, labored breathing, pain, an asthma attack, an epileptic episode, a seizure, or any combination thereof.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory system 120 and/or ambient pressure. In such implementations, the pressure sensor 132 can be coupled to or integrated in the respiratory device 122. The pressure sensor 132 can be, for example, a capacitive sensor, an electromagnetic sensor, a piezoelectric sensor, a strain-gauge sensor, an optical sensor, a potentiometric sensor, or any combination thereof.

The flow rate sensor 134 outputs flow rate data that can be stored in the memory device 114 and/or analyzed by the processor 112 of the control system 110. In some implementations, the flow rate sensor 134 is used to determine an air flow rate from the respiratory device 122, an air flow rate through the conduit 126, an air flow rate through the user interface 124, or any combination thereof. In such implementations, the flow rate sensor 134 can be coupled to or integrated in the respiratory device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof.

The temperature sensor 136 outputs temperature data that can be stored in the memory device 114 and/or analyzed by the processor 112 of the control system 110. In some implementations, the temperature sensor 136 generates temperatures data indicative of a core body temperature of the user 210 (FIG. 2), a skin temperature of the user 210, a temperature of the air flowing from the respiratory device 122 and/or through the conduit 126, a temperature in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof.

The microphone 140 outputs audio data that can be stored in the memory device 114 and/or analyzed by the processor 112 of the control system 110. The audio data generated by the microphone 140 is reproducible as one or more sound(s) during a sleep session (e.g., sounds from the user 210). The audio data form the microphone 140 can also be used to identify (e.g., using the control system 110) an event experienced by the user during the sleep session, as described in further detail herein. The microphone 140 can be coupled to or integrated in the respiratory device 122, the use interface 124, the conduit 126, or the user device 190.

The speaker 142 outputs sound waves that are audible to a user of the system 100 (e.g., the user 210 of FIG. 2). The speaker 142 can be used, for example, as an alarm clock or to play an alert or message to the user 210 (e.g., in response to an event). In some implementations, the speaker 142 can be used to communicate the audio data generated by the microphone 140 to the user. The speaker 142 can be coupled to or integrated in the respiratory device 122, the user interface 124, the conduit 126, or the user device 190.

The microphone 140 and the speaker 142 can be used as separate devices. In some implementations, the microphone 140 and the speaker 142 can be combined into an acoustic sensor 141, as described in, for example, WO 2018/050913 and WO 2020/104465, each of which is hereby incorporated by reference herein in its entirety. In such implementations, the speaker 142 generates or emits sound waves at a predetermined interval and/or frequency and the microphone 140 detects the reflections of the emitted sound waves from the speaker 142. The sound waves generated or emitted by the speaker 142 have a frequency that is not audible to the human ear (e.g., below 20 Hz or above around 18 kHz) so as not to disturb the sleep of the user 210 or the bed partner 220 (FIG. 2). Based at least in part on the data from the microphone 140 and/or the speaker 142, the control system 110 can determine a location of the user 210 (FIG. 2) and/or one or more of the sleep-related parameters described herein, such as, for example, a respiration signal, a respiration rate, an inspiration amplitude, an expiration amplitude, an inspiration-expiration ratio, a number of events per hour, a pattern of events, a sleep state, pressure settings of the respiratory device 122, or any combination thereof. In this context, a sonar sensor may be understood to concern an active acoustic sensing, such as by generating/transmitting ultrasound or low frequency ultrasound sensing signals (e.g., in a frequency range of about 17-23 kHz, 18-22 kHz, or 17-18 kHz, for example), through the air. The sonar sensor may be used in combination with a passive acoustic sensor, such that, for example, the active sonar sensor can detect bio-motion (such as respiration parameters) and the passive acoustic sensor can detect respiration sounds to determine with high confidence respiratory events such as apneas. Such a system may be considered in relation to WO 2018/050913 and WO 2020/104465 (which, as stated above, are incorporated by reference herein in their entirety).

In some implementations, the sensors 130 include (i) a first microphone that is the same as, or similar to, the microphone 140, and is integrated in the acoustic sensor 141 and (ii) a second microphone that is the same as, or similar to, the microphone 140, but is separate and distinct from the first microphone that is integrated in the acoustic sensor 141.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location of the user 210 (FIG. 2) and/or one or more of the sleep-related parameters described herein. An RF receiver (either the RF receiver 146 and the RF transmitter 148 or another RF pair) can also be used for wireless communication between the control system 110, the respiratory device 122, the one or more sensors 130, the user device 190, or any combination thereof. While the RF receiver 146 and RF transmitter 148 are shown as being separate and distinct elements in FIG. 1, in some implementations, the RF receiver 146 and RF transmitter 148 are combined as a part of an RF sensor 147. In some such implementations, the RF sensor 147 includes a control circuit. The specific format of the RF communication can be WiFi, Bluetooth, or the like.

In some implementations, the RF sensor 147 is a part of a mesh system. One example of a mesh system is a WiFi mesh system, which can include mesh nodes, mesh router(s), and mesh gateway(s), each of which can be mobile/movable or fixed. In such implementations, the WiFi mesh system includes a WiFi router and/or a WiFi controller and one or more satellites (e.g., access points), each of which include an RF sensor that the is the same as, or similar to, the RF sensor 147. The WiFi router and satellites continuously communicate with one another using WiFi signals. The WiFi mesh system can be used to generate motion data based on changes in the WiFi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or a combination thereof) that can be stored in the memory device 114. The image data from the camera 150 can be used by the control system 110 to determine one or more of the sleep-related parameters described herein. For example, the image data from the camera 150 can be used to identify a location of the user, to determine a time when the user 210 enters the bed 230 (FIG. 2), and to determine a time when the user 210 exits the bed 230. In some implementations, the camera 150 includes a wide angle lens or a fish eye lens.

The infrared (IR) sensor 152 outputs infrared image data reproducible as one or more infrared images (e.g., still images, video images, or both) that can be stored in the memory device 114. The infrared data from the IR sensor 152 can be used to determine one or more sleep-related parameters during a sleep session, including a temperature of the user 210 and/or movement of the user 210. The IR sensor 152 can also be used in conjunction with the camera 150 when measuring the presence, location, and/or movement of the user 210. The IR sensor 152 can detect infrared light having a wavelength between about 700 nm and about 1 mm, for example, while the camera 150 can detect visible light having a wavelength between about 380 nm and about 740 nm.

The PPG sensor 154 outputs physiological data associated with the user 210 (FIG. 2) that can be used to determine one or more sleep-related parameters, such as, for example, a heart rate, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user 210, embedded in clothing and/or fabric that is worn by the user 210, embedded in and/or coupled to the user interface 124 and/or its associated headgear (e.g., straps, etc.), etc.

The ECG sensor 156 outputs physiological data associated with electrical activity of the heart of the user 210. In some implementations, the ECG sensor 156 includes one or more electrodes that are positioned on or around a portion of the user 210 during the sleep session. The physiological data from the ECG sensor 156 can be used, for example, to determine one or more of the sleep-related parameters described herein.

The EEG sensor 158 outputs physiological data associated with electrical activity of the brain of the user 210. In some implementations, the EEG sensor 158 includes one or more electrodes that are positioned on or around the scalp of the user 210 during the sleep session. The physiological data from the EEG sensor 158 can be used, for example, to determine a sleep state of the user 210 at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, or any combination thereof. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user 210. The data output by the analyte sensor 174 can be stored in the memory device 114 and used by the control system 110 to determine the identity and concentration of any analytes in the breath of the user 210. In some implementations, the analyte sensor 174 is positioned near a mouth of the user 210 to detect analytes in breath exhaled from the user 210's mouth. For example, when the user interface 124 is a facial mask that covers the nose and mouth of the user 210, the analyte sensor 174 can be positioned within the facial mask to monitor the user 210's mouth breathing. In other implementations, such as when the user interface 124 is a nasal mask or a nasal pillow mask, the analyte sensor 174 can be positioned near the nose of the user 210 to detect analytes in breath exhaled through the user's nose. In still other implementations, the analyte sensor 174 can be positioned near the user 210's mouth when the user interface 124 is a nasal mask or a nasal pillow mask. In this implementation, the analyte sensor 174 can be used to detect whether any air is inadvertently leaking from the user 210's mouth. In some implementations, the analyte sensor 174 is a volatile organic compound (VOC) sensor that can be used to detect carbon-based chemicals or compounds. In some implementations, the analyte sensor 174 can also be used to detect whether the user 210 is breathing through their nose or mouth. For example, if the data output by an analyte sensor 174 positioned near the mouth of the user 210 or within the facial mask (in implementations where the user interface 124 is a facial mask) detects the presence of an analyte, the control system 110 can use this data as an indication that the user 210 is breathing through their mouth.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user 210's face, near the connection between the conduit 126 and the user interface 124, near the connection between the conduit 126 and the respiratory device 122, etc.). Thus, in some implementations, the moisture sensor 176 can be coupled to or integrated in the user interface 124 or in the conduit 126 to monitor the humidity of the pressurized air from the respiratory device 122. In other implementations, the moisture sensor 176 is placed near any area where moisture levels need to be monitored. The moisture sensor 176 can also be used to monitor the humidity of the ambient environment surrounding the user 210, for example, the air inside the bedroom.

The Light Detection and Ranging (LiDAR) sensor 178 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 178 can measure and map an area extending 5 meters or more away from the sensor. The LiDAR data can be fused with point cloud data estimated by an electromagnetic RADAR sensor, for example. The LiDAR sensor(s) 178 can also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

While shown separately in FIG. 1, any combination of the one or more sensors 130 can be integrated in and/or coupled to any one or more of the components of the system 100, including the respiratory device 122, the user interface 124, the conduit 126, the humidification tank 129, the control system 110, the user device 190, or any combination thereof. For example, the microphone 140 and speaker 142 is integrated in and/or coupled to the user device 190 and the pressure sensor 130 and/or flow rate sensor 132 are integrated in and/or coupled to the respiratory device 122. In some implementations, at least one of the one or more sensors 130 is not coupled to the respiratory device 122, the control system 110, or the user device 190, and is positioned generally adjacent to the user 210 during the sleep session (e.g., positioned on or in contact with a portion of the user 210, worn by the user 210, coupled to or positioned on the nightstand, coupled to the mattress, coupled to the ceiling, etc.).

The multi-compartment bladder 170 includes a plurality of separate and distinct compartments that can be at least partially inflated and/or at least partially deflated using fluid (e.g., air, water, gas, etc., or any combination thereof). The compartments of the multi-compartment bladder 170 can be inflated and/or deflated by the respiratory device 122 via the second conduit 172. The respiratory device 122 generates a pressure differential sufficient to at least partially inflate and/or deflate one or more of the compartments of the multi-compartment bladder 170.

In some implementations, the respiratory device 122 inflates one or more compartments of the multi-compartment bladder 170 such that the one or more compartments have a predetermined internal pressure to aid in supporting and/or moving a head of a user. On average, the weight of the head of the user is between about 4.5 kg and about 5 kg. Approximating the head of the user as a circle with a radius of about 10 cm, the pressure required to support the head is between about 1404 Pa (which is about 14.3 cm $H_2O$) and about 1560 Pa (which is about 15.9 cm $H_2O$). Thus, the predetermined internal pressure of the compartments of the multi-compartment bladder 170 can be between about 14.3 cm $H_2O$ and about 15.9 cm $H_2O$ to aid in supporting and/or moving the head of the user.

In some implementations, each of the compartments in the multi-compartment bladder 170 is directly, fluidly coupled or connected to the respiratory device 122 (e.g., using the second conduit 172). In other implementations, all or some of the compartments in the multi-compartment bladder 170 are fluidly coupled or connected together in series (e.g., such that fluid from the respiratory device 122 enters a first compartment and passes into a second compartment through the first compartment). Generally, inflation and/or deflation of the compartments of the multi-compartment bladder 170 cause the shape of the multi-compartment bladder 170 to change. In turn, the change in shape of the multi-compartment bladder 170 can cause corresponding movement of a portion of a user (e.g., a head) that is positioned on and/or in contact (e.g., directly or indirectly) with the multi-compartment bladder 170.

The valve 180 (FIG. 1) directs at least a portion of the pressurized air supplied by the respiratory device 122 to the first conduit 126 (which delivers the pressurized air to the interface 124) and/or the second conduit 172 (which delivers the pressurized air to the multi-compartment bladder 170). For example, the valve 180 can direct all of the pressurized air supplied from respiratory device 122 to the first conduit 126 or the second conduit 172. Alternatively, the valve 180 can direct a first portion and/or volume of the supplied pressurized air to the first conduit 126 and direct a second portion and/or volume of the supplied pressurized air to the second conduit 172. The first portion and/or volume and the second portion and/or volume can be the same or different. For example, the first portion and/or volume directed to the first conduit 126 can be between about 1.1 and 10 times greater than the second portion and/or volume directed to the second conduit 172. Conversely, the second portion and/or volume directed to the second conduit 172 can be between about 1.1 and 10 times greater than the first portion and/or volume directed to the first conduit 126.

In some implementations, actuation (e.g., opening and/or closing) of the valve 180 can be controlled pneumatically using, for example, the control system 110 (FIG. 1), which can be communicatively coupled to the valve 180 (e.g., using a wired connection or a wireless connection). Alternatively, the valve 180 can include a solenoid that can be electrically energized and/or de-energized using the control system 110 (FIG. 1) to actuate (e.g., open and/or close) the valve 180.

In some implementations, the valve 180 is a three-way T-pattern or T-port ball valve configured such that the valve 180 can direct portions of the supplied pressurized air from the respiratory device 122 to both the first conduit 126 and the second conduit 172 at the same time. In other implementations, the valve 180 is a three-way L-pattern or L-port ball valve that directs the supplied pressurized to either the first conduit 126 or the second conduit 172, but not both at the same time. Alternatively, the valve 180 can be a butterfly valve, a choke valve, a gate valve, a globe valve, a plug valve, a solenoid valve, or any other suitable type of valve for directing pressurized air to one or both of the first conduit 126 and the second conduit 172 either at the same time or independently.

In some implementations, the first conduit 126 has a first diameter and the second conduit 172 has a second diameter that is less than the first diameter (e.g., 10% smaller, 25% smaller, 50% smaller, 75% smaller, 100% smaller, 200% smaller, 300% smaller, etc.). In such implementations, if the same volume of air is directed by the valve 180 to the first conduit 126 and the second conduit 172 (e.g., the volume of pressurized air supplied by the respiratory device 122 is divided equally), the pressure of the air in the second 172 is higher than the pressure of the air in the first conduit 126 due to the smaller diameter of the second conduit 172 relative to the first conduit 126.

The user device 190 (FIG. 1) includes a display device 192. The user device 190 can be, for example, a mobile device such as a smart phone, a tablet, a laptop, or the like. Alternatively, the user device 190 can be a television (e.g., a smart television) or another smart home device. In some implementations, the external device is a wearable device (e.g., a smart watch). The display device 192 is generally used to display image(s) including still images, video images, or both. In some implementations, the display device 192 acts as a human-machine interface (HMI) that includes a graphic user interface (GUI) configured to display the image(s) and an input interface. The display device 192 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 190. In some implementations, one or more user devices can be used by and/or included in the system 100.

While the control system 110 and the memory device 114 are described and shown in FIG. 1 as being a separate and distinct component of the system 100, in some implementations, the control system 110 and/or the memory device 114 are integrated or distributed in the user device 190 and/or the respiratory device 122. Alternatively, in some implementations, the control system 110 or a portion thereof (e.g., the processor 112) can be located in a cloud (e.g., integrated in a server, integrated in an Internet of Things (IOT) device, connected to the cloud, edge cloud processing, etc.), in one or more servers (e.g., remote servers, local servers, etc.), or any combination thereof.

While system 100 is shown as including all of the components described above, more or fewer components can be included in a system for generating physiological data and determining sleep-related parameters according to implementations of the present disclosure. For example, a first alternative system includes the control system 110 and at least one of the one or more sensors 130. As another example, a second alternative system includes the respiratory device 122, the interface 124, the first conduit 126, at least one of the one or more sensors 130, and the user device 190. As yet another example, a third alternative system includes the control system 110, at least one of the one or more sensors 130, and the user device 190. Thus, various systems for determining sleep-related parameters associated with a sleep session can be formed using any portion or portions of the components shown and described herein and/or in combination with one or more other components.

Figure 3:
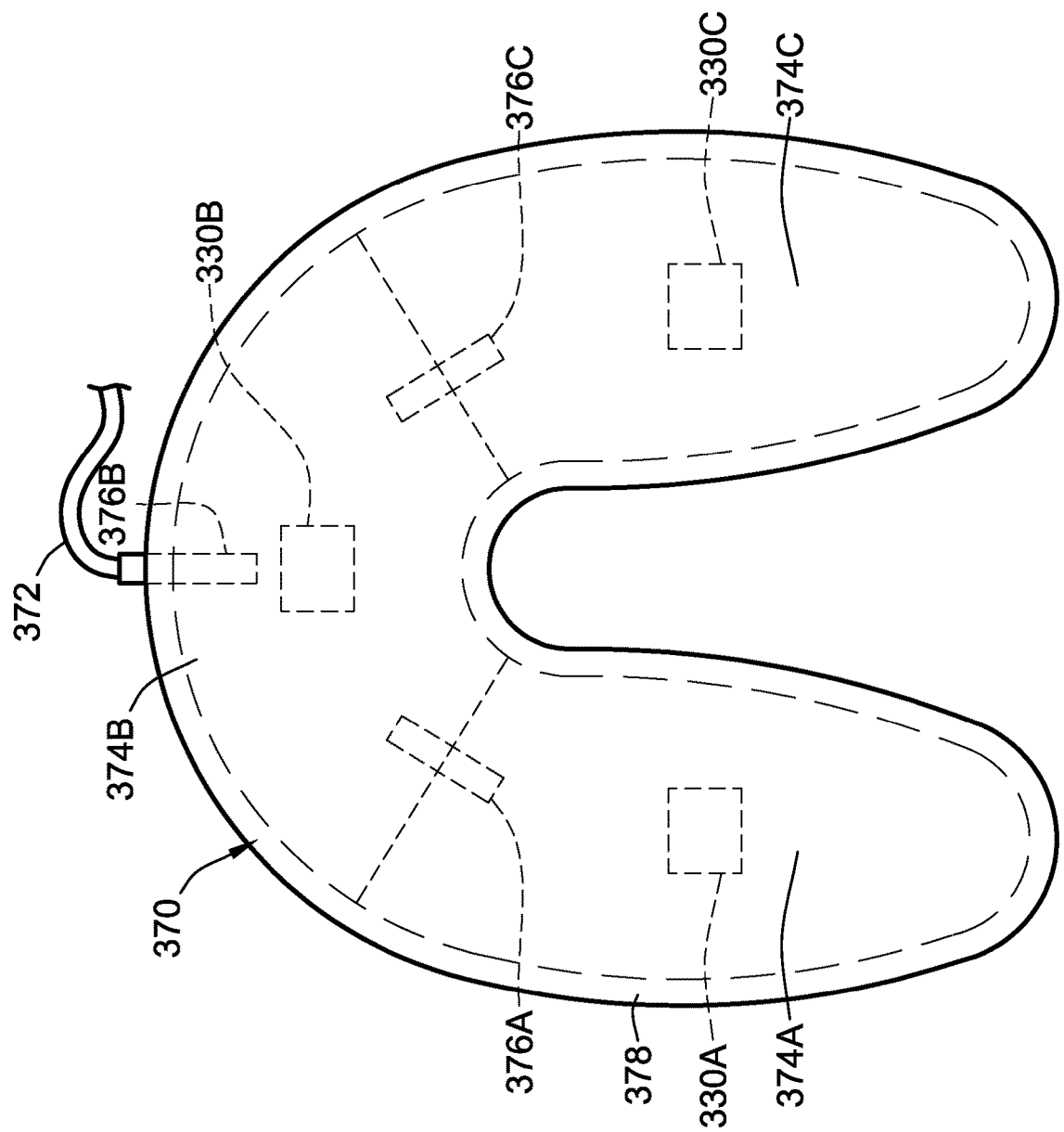
FIG. 3 is a top view of a generally U-shaped multi-compartment bladder of the system of FIG. 1 with a plurality of compartments fluidly coupled in series, according to some implementations of the present disclosure.

Referring to FIG. 3, a generally U-shaped multi-compartment bladder 370 that is the same as, or similar to, the multi-compartment bladder 170 (FIG. 1) includes a plurality of separate and distinct compartments 374A-374C, a plurality of valves 376A-376C, and a plurality of sensors 330A-330C.

The multi-compartment bladder 370 is fluidly coupled or connected to a respirator device that is the same as, or similar to, the respiratory device 122 (FIG. 1) using a tube 372 that is the same as, or similar to, the second conduit 172 (FIG. 1) described above. The tube 372 delivers pressurized air from the respirator device to the multi-compartment bladder 170 to cause inflation of at least a portion of the multi-compartment bladder 370. More specifically, the tube 372 is coupled to a first valve 376B, which controls the flow of fluid (e.g., air) in and/or out of the multi-compartment bladder 370.

In some implementations, the first valve 376B is a bi-directional valve that automatically controls fluid flow in either direction (e.g., flow into and out of the multi-compartment bladder 370). For example, the first valve 376B can open or close in response to a predetermined pressure differential. Alternatively, in some implementations, opening and/or closing of the first valve 376B can be pneumatically controlled using, for example, the control system 110 (FIG. 1), which can be communicatively coupled to the first valve 376B (e.g., using a wired connection or a wireless connection). Further, while the first valve 376B as shown as being in direct fluid communication with the second compartment 374B, more generally, the first valve 376B that receives fluid from the second tube 372 can be in direct communication with any of the compartments 374A-374C.

The plurality of compartments 374A-374C are fluidly coupled or connected to one another in series via a second valve 376A and a third valve 376C that are the same as, or similar to, the first valve 376B. The second valve 376A is positioned between the first compartment 374A and the second compartment 374B, and thus controls flow between the second compartment 374B and the first compartment 374A. For example, if the first valve 376B is open and the second valve 376B is closed, the second compartment 374B can be inflated or deflated via the tube 372, whereas the first compartment 374A will not be inflated or deflated. Conversely, if both the first valve 376B and the second valve 376A are open, fluid can flow from the second compartment 374B and into the first compartment 374A to cause inflation or deflation. The third valve 376C is positioned between the second compartment 374B and the third compartment 374C and operates in the same, or similar, manner as the second valve 376A.

In some implementations, one or more of the valves 376A-376C is a one-way check valve that permits fluid flow in only one direction (e.g., a ball check valve, a diaphragm check valve, a swing check valve, etc.) For example, the valve 376A positioned between the first compartment 374A and the second compartment 374B can be a check valve that permits fluid to flow from the second compartment 374B to the first compartment 374A, but not from the first compartment 374A to the second compartment 374B. Alternatively, one or more of the valves 376A-376C is a two-way or bi-directional valve that permits fluid to flow in both directions. For example, the valve 376A positioned between the first compartment 374A and the second compartment 374B can be a two-way valve that permits fluid to flow from the first compartment 374A to the second compartment 374B, and vice versa.

Each of the valves 376A-376C can be actuated (e.g., opened or closed) in a predetermined sequence to achieve a desired inflation level for each compartment 374A-374C. For example, to inflate the first compartment 374A more than the second compartment 374B, fluid is first pumped into the second compartment 374B via the tube 372, which thereafter enters the first compartment 374A via the second valve 376A until a predetermined inflation level is reached, and thereafter the second valve 376A can be closed and the second compartment 374B is deflated via the first valve 376B. In this manner, each of the separate and distinct compartments 374A-374C can be inflated by the same or different amounts by controlling the flow of fluid using valves 376A-376C (e.g., the second compartment 374B can be inflated more than the first compartment 374A and/or the third compartment 374C, or vice versa). In some implementations, the valves 376A-376C are passive and do not need to be activated.

In some implementations, one or more of the compartments 374A-374C includes one or more relief valves for venting pressurized air from one or more of the compartments 374A-374C to the atmosphere to at least partially deflate the one or more compartments 374A-374C. The relief valves can be the same as, or integrated in, the valves 376A-376C described herein, or separate and distinct from the valves 376A-376C. For example, the first valve 376B can include a relief valve for venting pressurized air from one or more of the compartments 374A-374C. Alternatively, each of the compartments 374A-374C can include a separate and distinct relief valve to for individually deflating each of the compartments 374A-374C.

The plurality of sensors 330A-330C that are the same as, or similar to, the one or more sensors 130 (FIG. 1) described above. As shown, a first sensor 330A is coupled to or disposed within the first compartment 374A, a second sensor 330B is coupled to or disposed within the second compartment 374B, and a third sensor 330C is coupled to or disposed within the third compartment 374C. In some implementations, each of the sensors 330A-330C are pressure sensors configured to output pressure data indicative of a pressure within each of the compartments 374A-374B, pressure data indicative of an external pressure applied to an outer portion of the multi-compartment bladder 370 (e.g., by a head of a user), or both. Data from the sensors 330A-330C can be used by the control system 110 (FIG. 1) to determine whether to inflate or deflate one or more of the compartments 374A-374C (e.g., by comparing the pressure in each compartment 374A-374C to a predetermined threshold pressure). For example, data from the sensors 330A-330C can be used to determine an inflation percentage of each compartment 374A-374C compared to a maximum volume of each compartment 374A-374C (e.g., 10% inflated, 50% inflated, 75% inflated, 100% inflated, etc.) While each compartment 374A-374C is shown as including one of the sensors 330A-330C in FIG. 3, each compartment 374A-374C can include no sensors or a plurality of sensors, including a plurality of different types of sensors (e.g., a force sensor, an air pressure sensor and a temperature sensor).

As shown in FIG. 3, in some implementations, an outer cushion 378 generally surrounds at least a portion the compartments 374A-374C such that a user of the multi-compartment bladder 370 does not come in direct contact with an outer or exterior surface of the compartments 374A-374C. The outer cushion 378 can include, for example, a fabric material, a foam or memory-foam material, down, feathers, a gel material, or any combination thereof. In some implementations, the outer cushion 378 is removable and includes an opening for receiving the compartments 374A-374C therein that can be closed, for example, using hook and loop fasteners, a zipper, etc. In such implementations, the cushion 378 and the multi-compartment bladder 370 can be collectively referred to as a pillow.

Figure 4:
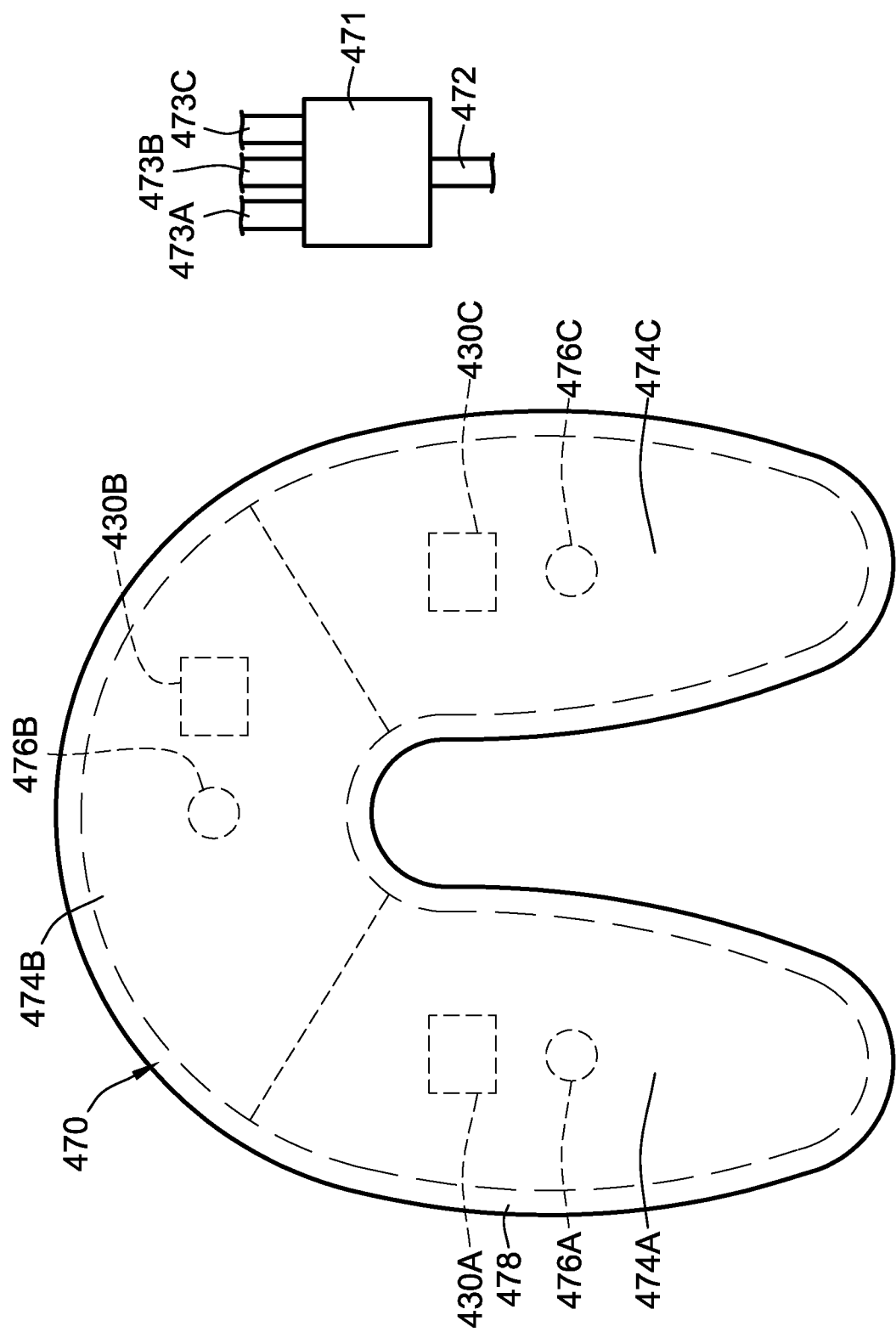
FIG. 4 is a top view of a generally U-shaped multi-compartment bladder of the system of FIG. 1, according to some implementations of the present disclosure.

Referring to FIG. 4, a generally U-shaped multi-compartment bladder 470 that is similar to the multi-compartment bladder 370 (FIG. 3) includes a manifold 471, a plurality of conduits 473A-473C, a plurality of separate and distinct compartments 474A-474C, a plurality of valves 476A-476C, and a plurality of sensors 430A-430C. In some implementations, the multi-compartment bladder 470 can be at least partially surrounded by and/or disposed within an outer cushion 478 that is the same as, or similar to, the outer cushion 378 (FIG. 3).

The compartments 474A-474C of the multi-compartment bladder 470 differ from the compartments 374A-374C of the multi-compartment bladder 370 (FIG. 3) in that the compartments 474A-474C are not fluidly connected or coupled in series. Instead, each of the compartments 474A-474C is separately and independently in fluid communication with the respirator device via the conduits 473A-473C and the manifold 471. The manifold 471 is coupled to and in fluid communication with a tube 472 that is the same as, or similar to, the tube 372 (FIG. 3) and the second conduit 172 (FIG. 1). The manifold 471 divides the air flow from the tube 472 to each of the conduits 473A-473C. Each of the conduits 473A-473C is coupled to a corresponding one of the valves 476A-476C, which independently control inflation and/or deflation of each of the compartments 474A-474C.

In some implementations, the manifold 471 selectively diverts a portion of the fluid (e.g., air) from the tube 472 to one or more of the conduits 473A-473C in the same or similar manner as the valves 476A-476C. For example, the manifold 471 can cause at least a portion of the fluid from the tube 472 to be directed to none of the conduits 473A-473C, all of the conduits 473A-473C, one of the conduits 473A-473C, or two of the conduits 473A-473C. In such implementations, the multi-compartment bladder 470 does not include the valves 476A-476C. Instead, the conduits 473A-473C are coupled to and are in directly communication with a respective one of the compartments 474A-474C.

In some alternative implementations, the multi-compartment bladder 470 does not include the manifold 471 and the tube 472. Instead, in such implementations, each of the conduits 473A-473C can be directly and individually coupled to the respirator device via a conduit or tube that is the same as, or similar to, the tube 472.

While the multi-compartment bladder 370 (FIG. 3) and the multi-compartment bladder 470 (FIG. 4) are both shown and described as including three separate and distinct compartments, more generally, the multi-compartment bladder 370 and/or the multi-compartment bladder 470 can include any suitable number of separate and distinct compartments (e.g., 1 compartment, 2 compartments, 5 compartments, 10 compartments, 20 compartments, 50 compartments, 100 compartments, etc.) Moreover, while the multi-compartment bladder 370 (FIG. 3) and the multi-compartment bladder 470 (FIG. 4) are both shown and described as including the same number of valves and the number of compartments, more generally, the multi-compartment bladder 370 (FIG. 3) and/or the multi-compartment bladder 470 (FIG. 4) can include different numbers of valves and compartments (e.g., three compartments and six valves, three compartments and two valves, etc.)

Figure 5:
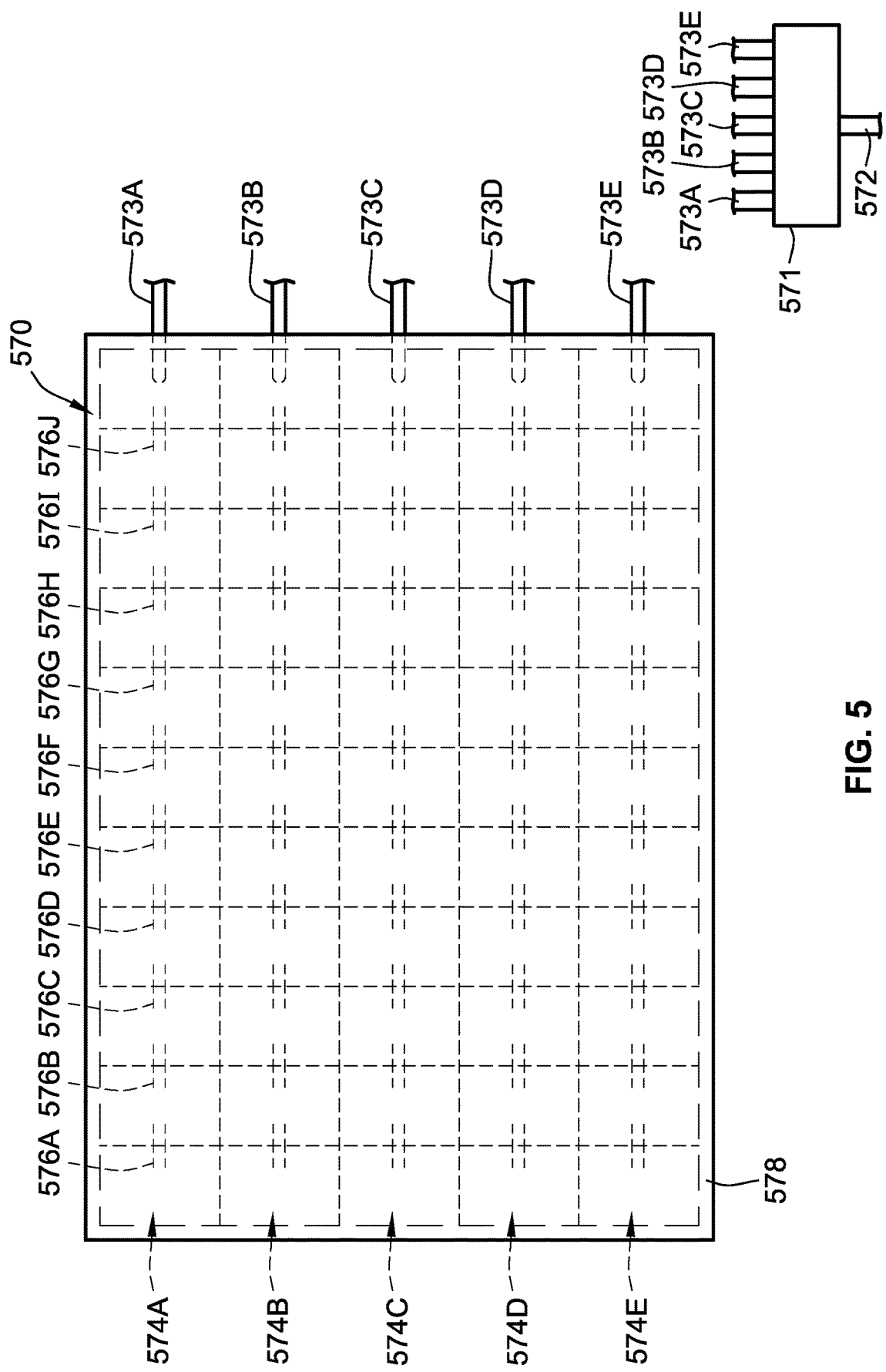
FIG. 5 is a top view of a generally rectangular multi-compartment bladder of the system of FIG. 1, according to some implementations of the present disclosure.

Referring to FIG. 5, a generally rectangular multi-compartment bladder 570 that is similar to the multi-compartment bladder 370 (FIG. 3) and the multi-compartment bladder 470 (FIG. 4) includes a manifold 571, a plurality of conduits 573A-E, a plurality of a plurality of rows of compartments 574A-574E, a plurality of valves 576A-576E. In some implementations, the multi-compartment bladder 570 can be at least partially surrounded by and/or disposed within an outer cushion 578 that is the same as, or similar to, the outer cushion 378 (FIG. 3).

The manifold 571 is the same as, or similar to, the manifold 471 of the multi-compartment bladder 470 (FIG. 4) and is coupled to and in fluid communication with a tube 572 that is the same as, or similar to, the second conduit 172 (FIG. 1). Each of the plurality of rows of compartments 574A-574E is fluidly coupled or connected to the manifold 571 via a corresponding one of a plurality of conduits 573A-573E. Further, each of the compartments in each of the plurality of rows 574A-574E are fluidly connected or coupled in series. For example, as shown, the compartments in the first row of compartments 574A are fluidly coupled or connected in series via a plurality of valves 576A-576J. Actuating the valves 576A-576J (e.g., pneumatically via the control system 110 (FIG. 1)) permits each of the plurality of compartments to be inflated or deflated to a predetermined inflation level. In some implementations, the valves 576A-576J are passive and do not need to be actuated.

While the compartments of the multi-compartment bladder 570 are shown as being arranged in a matrix including five rows of compartments where each row includes ten compartments, more generally, the multi-compartment bladder 570 can have any ratio of compartments per row to the total number of rows (e.g., 2:1, 2:3, 1:1, 5:1, 10:1, etc.) Further, the multi-compartment bladder 570 can have any suitable number of compartments (e.g., 10 compartments, 50 compartments, 100 compartments, 500 compartments, etc.) Further still, while each of the compartments in the multi-compartment bladder 570 are shown as having generally the same size and/or shape, other types and combinations of shapes (e.g., circular shapes, triangular shapes, polygonal shapes, etc. or any combination thereof) and/or relative sizes are expressly contemplated.

While the system 100 (FIG. 1) is shown as including the multi-compartment bladder 170, more generally, the system can include any one of the multi-compartment bladder 370 (FIG. 3), the multi-compartment bladder 470 (FIG. 4), and the multi-compartment bladder 570 (FIG. 5), or any combination thereof.

Figure 6A:
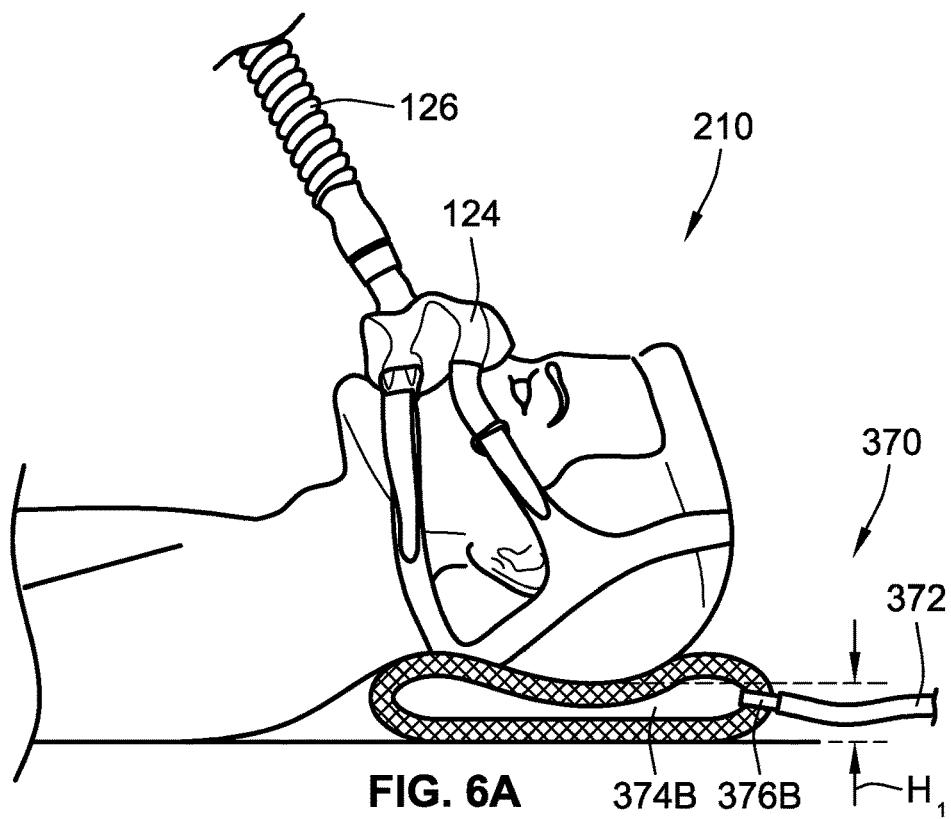
FIG. 6A is a partial cross-sectional view of the multi-compartment bladder of FIG. 3 and a side view of a user in a first position, according to some implementations of the present disclosure.
Figure 6B:
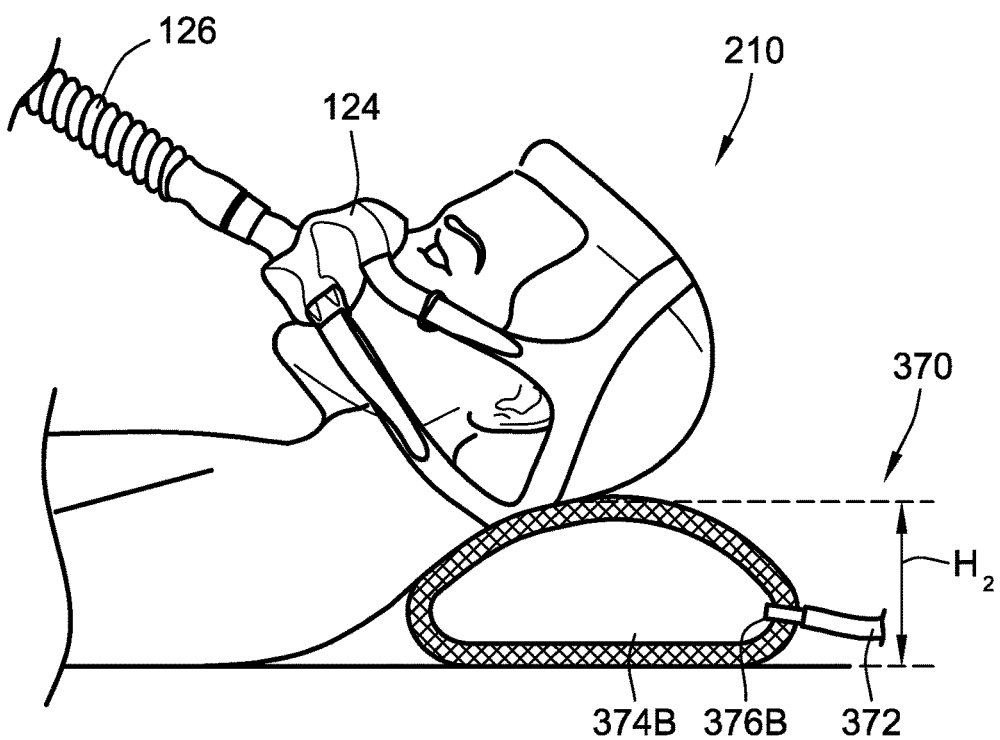
FIG. 6B is a partial cross-section view of the multi-compartment bladder of FIG. 3 and a side view of the user in a second position, according to some implementations of the present disclosure.

As described herein, the multi-compartment bladder 170 (FIG. 1), the multi-compartment bladder 370 (FIG. 3), the multi-compartment bladder 470 (FIG. 4), and the multi-compartment bladder 570 (FIG. 5) can be used to adjust a position of a user (e.g., a head of the user) during a sleep session by selectively inflating and/or deflating one or more of the compartments of the multi-compartment bladder. For example, referring to FIG. 6A, the user 210 is shown lying on the multi-compartment bladder 370 (FIG. 3) in a first position while wearing the interface 124 that is coupled to the respiratory device 122 (FIG. 1) via the tube 372. As shown, the second compartment 374B of the multi-compartment bladder 370 has a first height $H_1$ that is based on the volume of fluid (e.g., air) within the second compartment 374B and the external pressure applied by the head of the user 210. Referring to FIG. 6B, directing pressurized air from the respiratory device 122 (FIG. 1) into the second compartment 374B, via the tube 372, causes the second compartment 374B to inflate and/or expand (countering pressure from the head of the user 210) such that the second compartment 374B has a second height $H_2$ (FIG. 6B) that is greater than the first height $H_1$ (FIG. 6A) (e.g., at least 1.5 times greater than the first height, at least 2 times greater than the first height, etc.) As shown by a comparison between FIG. 6A and FIG. 6B, inflating the second compartment 374B causes the user 210 to move from the first position (FIG. 6A) to the second position (FIG. 6B). Specifically, the head of the user 210 moves or tilts forward about a transverse or horizontal axis when moving from the first position (FIG. 6A) to the second position (FIG. 6B). In the second position, the head of the user 210 is tilted upwards and forward relative to the first position, which can aid in opening and/or clearing the airway of the user 210, thereby aiding in preventing an event (e.g., snoring, apnea, etc.) from occurring and/or aiding in treating an event that the user is currently experiencing during a sleep session.

Figure 6C:
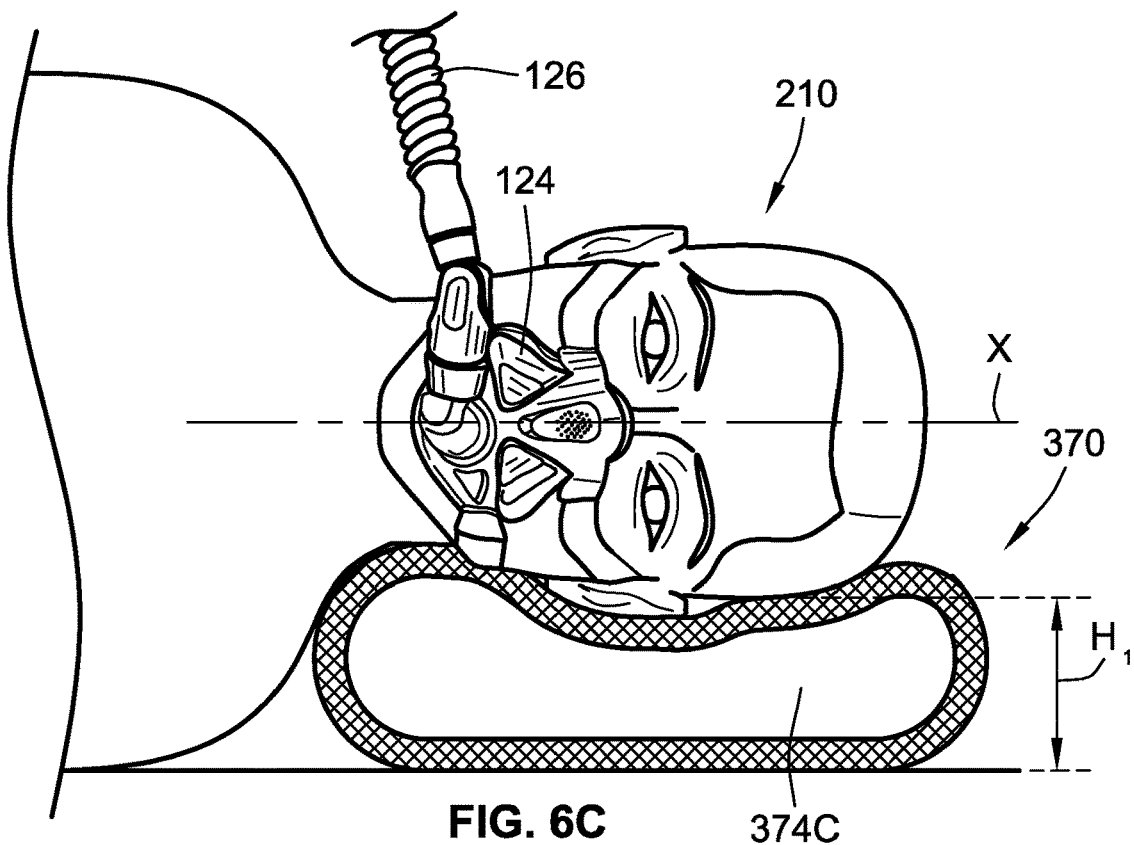
FIG. 6C is a partial cross-sectional view of the multi-compartment bladder of FIG. 3 and a side view of a user in a first position, according to some implementations of the present disclosure.
Figure 6D:
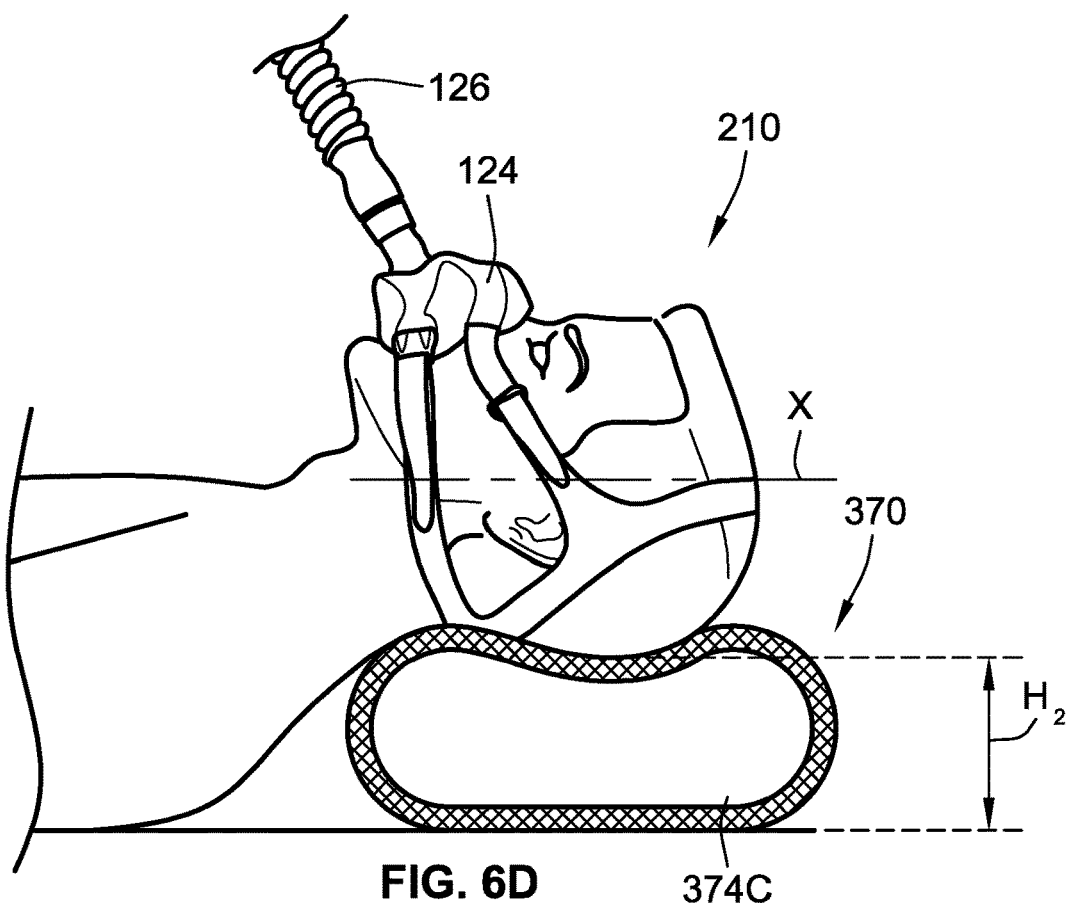
FIG. 6D is a partial cross-section view of the multi-compartment bladder of FIG. 3 and a side view of the user in a second position, according to some implementations of the present disclosure.

Similarly, referring to FIG. 6C, the user 210 is shown laying on the multi-compartment bladder 370 (FIG. 3) in a third position while wearing the interface 124. In this third position, the user 210 is laying on their side, which can cause the interface 124 to partially disengage the user 210, causing air to leak from the interface 124. Air leakage is undesirable because it can cause noise(s) that disturbs the sleep of the user 210 and/or the bed partner 220, cause skin irritation, and/or generally reduce the volume of air that is delivered to the airway of the user 210. In this position, the third compartment 374C has a first height $H_1$ that is based on the volume of fluid (e.g., air) within the third compartment 374C and the external pressure applied by the head of the user 210. Referring to FIG. 6D, directing pressurized air from the respiratory device 122 (FIG. 1) into the third compartment 374C, via the tube 372 (FIG. 3), causes the third compartment 374C to inflate or expand (countering pressure from the head of the user 210) such that the third compartment 374C has a second height $H_2$ (FIG. 6D) that is greater than the first height $H_1$ (FIG. 6C) (e.g., at least 1.5 times greater than the first height, at least 2 times greater than the first height, etc.) As shown by a comparison between FIG. 6C and FIG. 6D, inflating the third compartment 374C causes the user 210 to move from the third position (FIG. 6A) to a fourth position (FIG. 6B). The head of the user 210 rotates in a circular fashion about a longitudinal axis X when moving between the third position and the fourth position (e.g., the head moves side-to-side). Moving the user 210 from the third position to the fourth position causes the user 210 to be positioned generally on their back as opposed to generally on their side, which can improve the engagement (e.g., seal) between the interface 124 and the face of the user 210, thereby reducing or preventing air leakage from the interface 124.

Figure 7A:
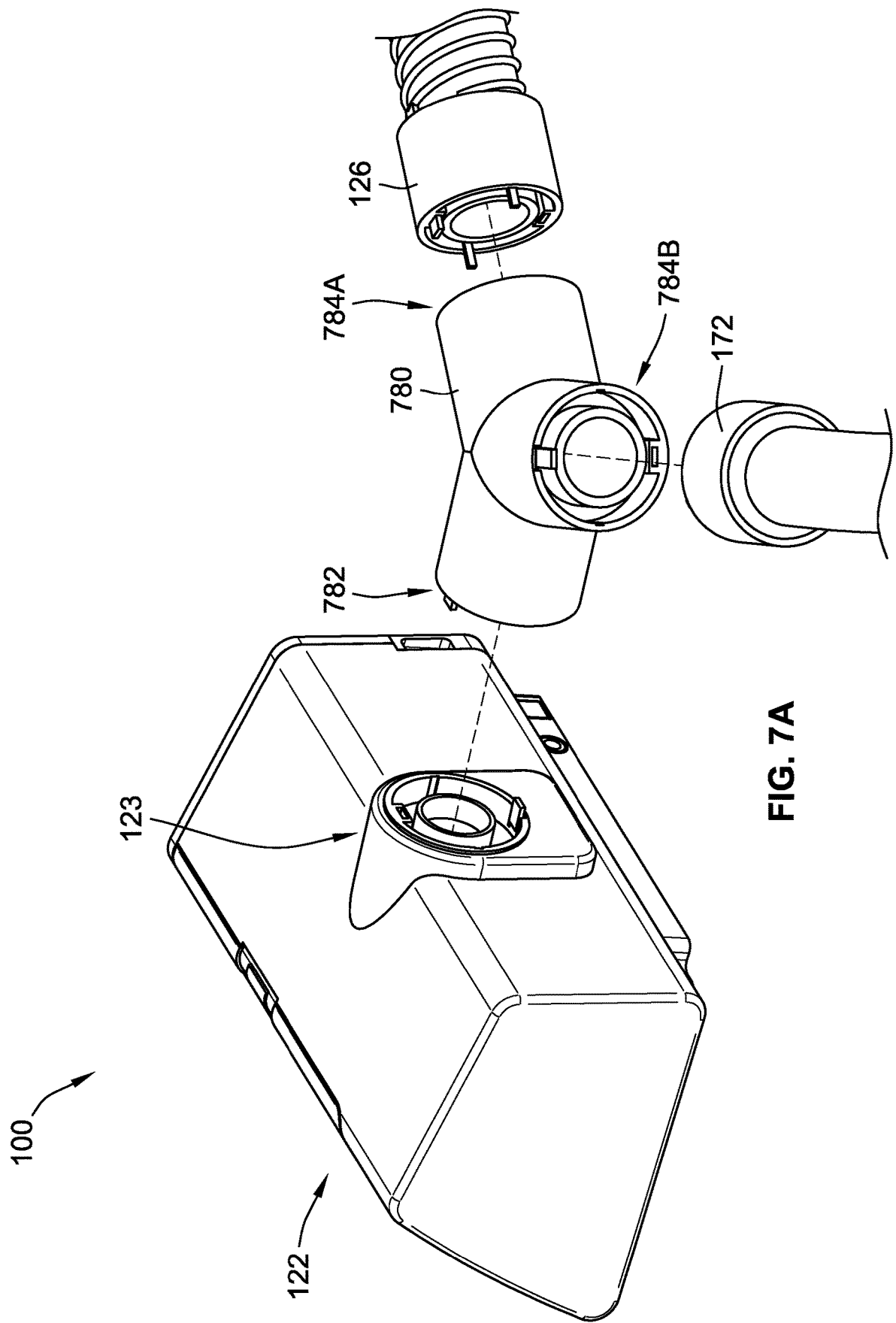
FIG. 7A is a partially exploded perspective view of a respirator device, a valve, a first tube, and a second tube of the system of FIG. 1, according to some implementations of the present disclosure.

Referring to FIG. 7A, in some implementations, the system 100 includes a valve 780 that is the same as, or similar to, the valve 180 (FIG. 1) described herein. As shown, the respiratory device 122 includes an outlet 123 to permit the pressurized air generated therein to exit the respiratory device 122. The valve 780 includes an inlet 782 that is coupled to and in fluid communication with the outlet 123. The valve 780 also includes a first outlet 784A that is coupled to and in fluid communication with the first conduit 126, and a second outlet 784B that is coupled to and in fluid communication with the second conduit 172. The inlet 782 of the valve 780 can be coupled (e.g., removably coupled or permanently coupled) to the outlet 123 of the respirator device 123 using a variety of mechanisms, such as, for example, a press fit, a click fit, an interference fit, a locking collar, a pin and sleeve connection, a tongue and groove connection, a threaded connection, a magnetic connection, or any combination thereof. The first conduit 126 and the second conduit 172 can be coupled to the first outlet 784A and the second outlet 784B of the valve 780, respectively, using the same or similar mechanisms or different mechanisms.

Figure 7B:
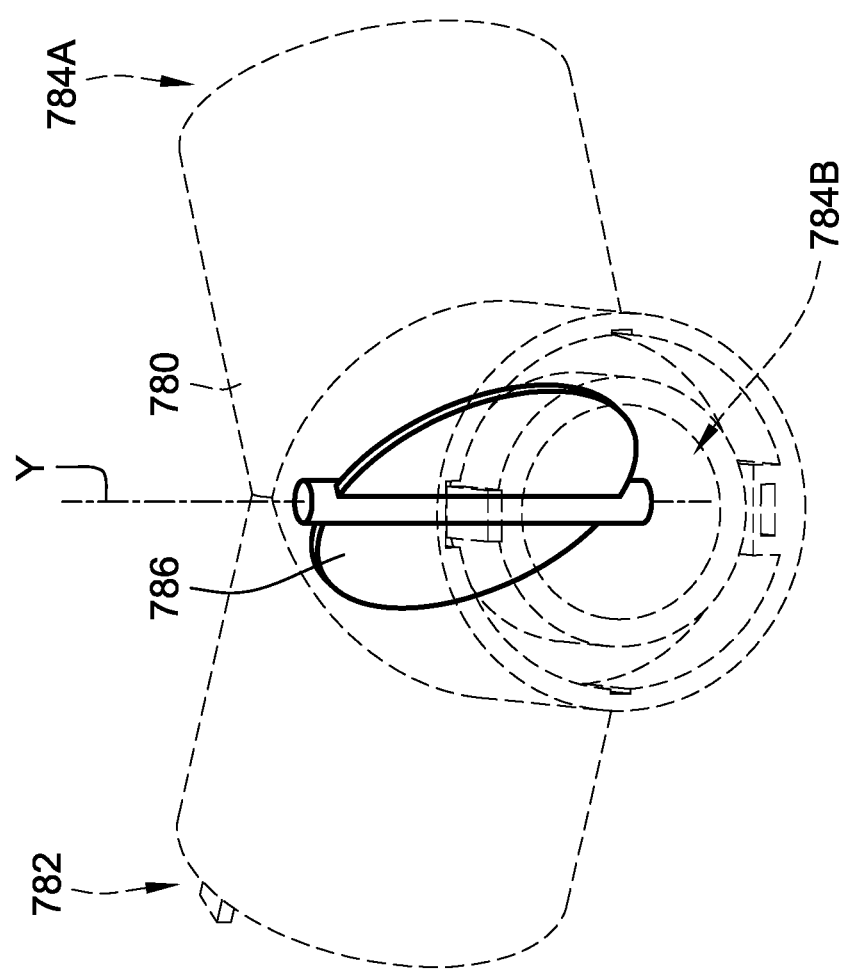
FIG. 7B is a partial perspective view of an internal disk of the valve of FIG. 7A, according to some implementations of the present disclosure.

Referring to FIG. 7B, in some implementations, the valve 780 is a butterfly valve and includes an internal disk 786. The internal disk 786 is rotatable about a vertical axis Y such that the internal disk can direct the pressurized air entering the inlet 782 to only the first outlet 784A, to only the second outlet 784B, or neither the first outlet 784A nor the second outlet 784B. Alternatively, the internal disk 786 can be rotated about the vertical axis Y such that the internal disk 786 directs a first volume of the pressurized air entering the inlet 782 to the first outlet 784A and a second volume of the pressurized air entering the inlet 782 to the second outlet 784B at the same time. The internal disk 786 can be rotated and positioned relative to the first outlet 784A and the second outlet 784B such that the first volume is the same as the second volume, the first volume is greater than the second volume, or the second volume is greater than the first volume. The internal disk 786 can be rotated or actuated pneumatically or electronically using the control system 110 (FIG. 1).

In some implementations, the internal disk 786 and/or the valve 780 can be modulated to alternatively deliver pressurized air to the first outlet 784A and the second outlet 784B. The causes the internal disk 786 to rotate back and forth (e.g., every 2 seconds, every 1 second, every 0.5 seconds, etc.). As such, the modulation allows for the pressurized air to generally be continuously delivered to the user 210 and also be used to inflate the multi-compartment bladder 170. That is, even with the pressurized air being diverted from the first conduit 126 intermittently, if the modulation is fast enough, the airway of the user 210 will remain sufficiently open while allowing for the multi-compartment bladder 170 to also be inflated.

While the valve 780 is shown and described as being a butterfly valve, alternatively, in some implementations, the valve 780 is a ball valve including a T-shaped port for directing pressurized air to one or both of the first outlet 784A and the second outlet 784B or an L-shaped port for directing the pressurized air to the first outlet 784A or the second outlet 784B, but not both simultaneously.

Figure 8A:
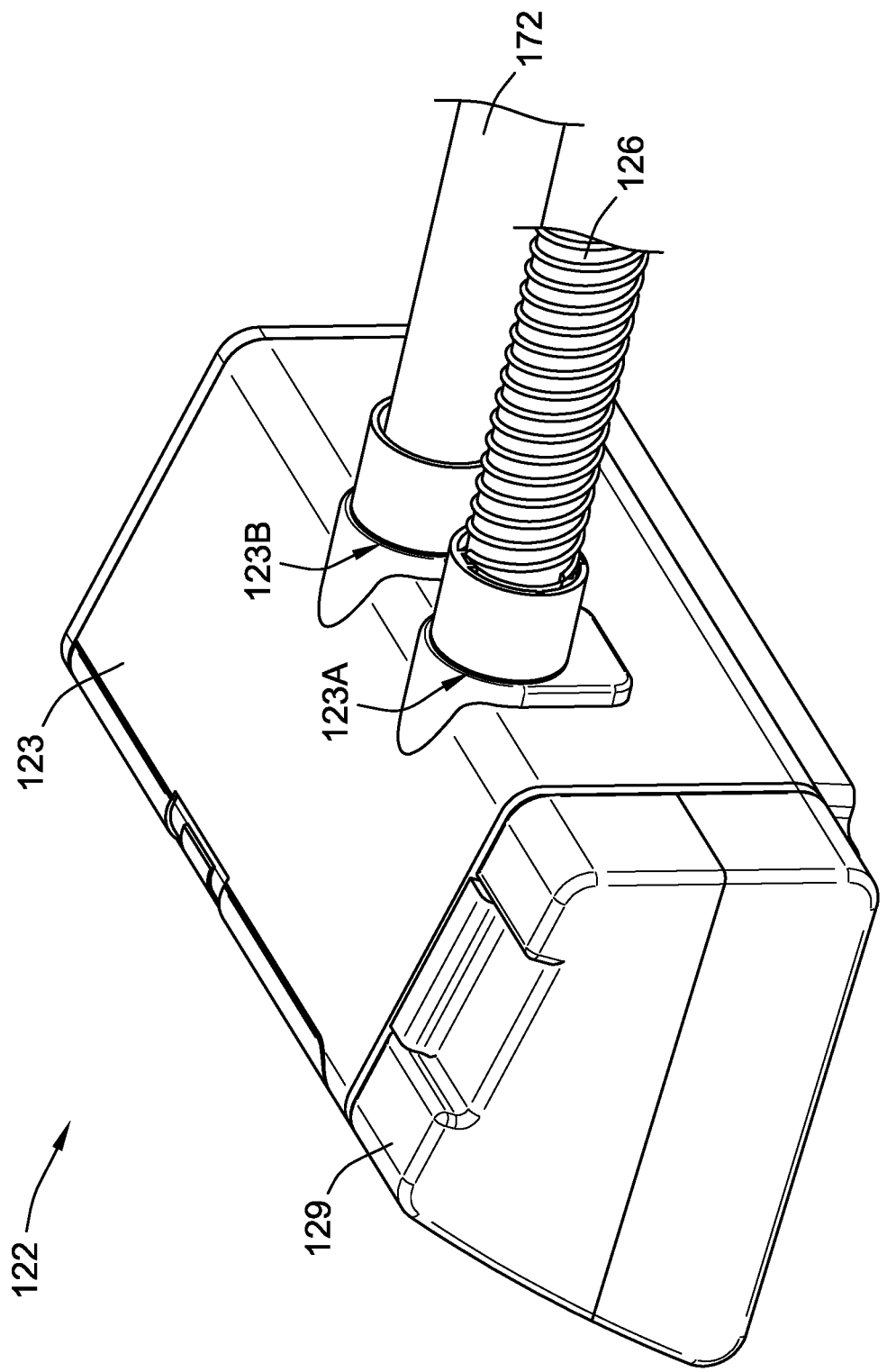
FIG. 8A is a perspective view of a respirator device, a first tube, and a second tube of the system of FIG. 1, according to some implementations of the present disclosure.
Figure 8B:
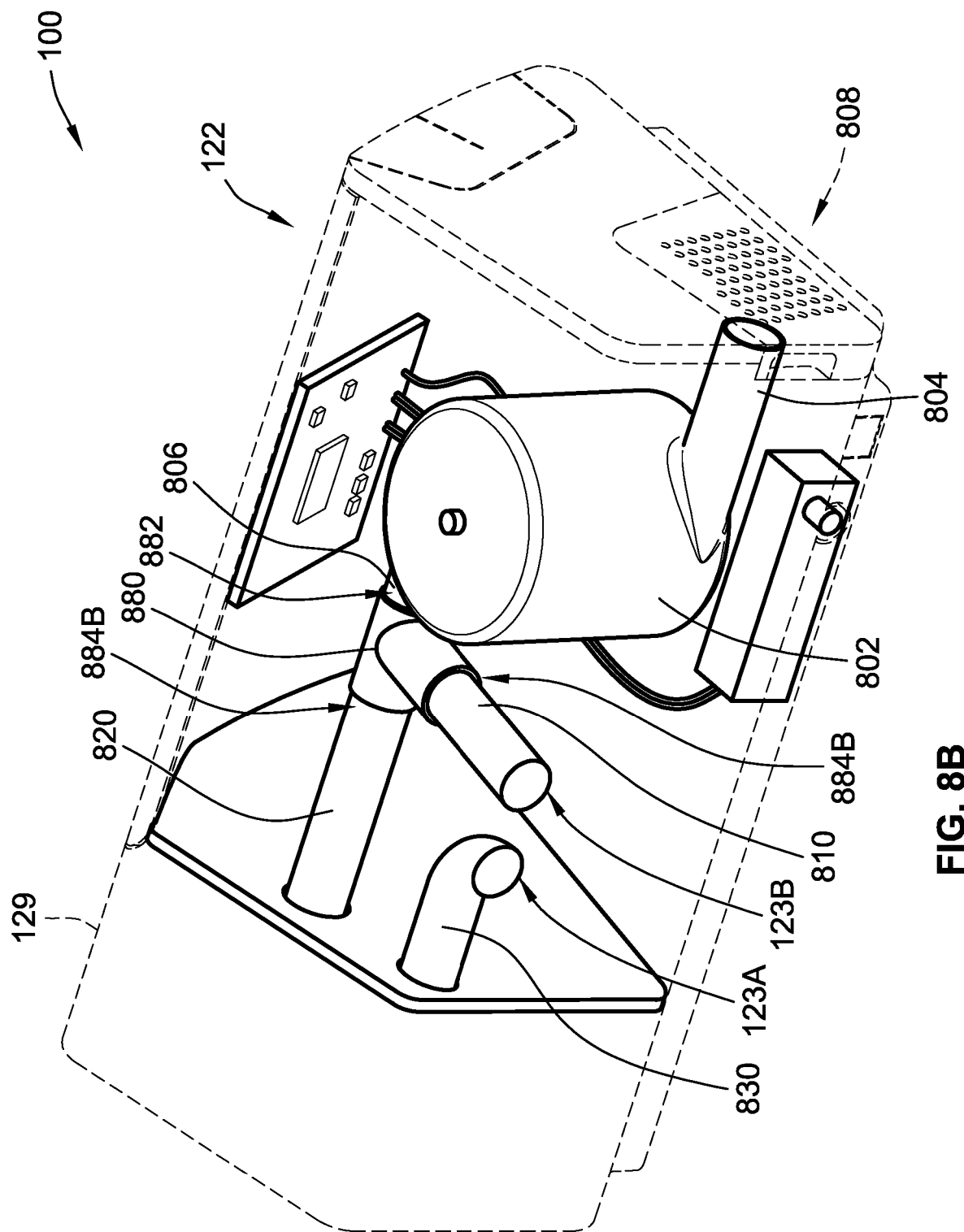
FIG. 8B is a perspective view of the respirator device of FIG. 8A with a portion of the outer housing removed for illustrative purposes, according to some implementations of the present disclosure.

Referring to FIGS. 8A and 8B, in some implementations, the system 100 includes a valve 880 (FIG. 8B) that is the same as, or similar to, the valve 180 (FIG. 1) described herein. In such implementations, the respiratory device 122 includes a first outlet 123A and a second outlet 123B to permit the pressurized air generated therein to exit the respiratory device 122. The first conduit 126 is coupled to and in fluid communication with the first outlet 123A. Similarly, the second conduit 172 is coupled to and in fluid communication with the second outlet 123B.

Referring to FIG. 8B, the respiratory device 122 includes a blower motor 802, a motor intake 804, and a motor outlet 806. The motor intake 804 is in fluid communication with the atmosphere through an air inlet 808 of the respiratory device 122. The motor outlet 806 is coupled to and in fluid communication with the valve 880, as described in further detail below. During operation of the respiratory device 122, the blower motor 802 causes air to flow through the motor and through the motor outlet 806, and eventually through the first outlet 123A and/or the second outlet 123B.

The valve 880 differs from the valve 780 (FIGS. 7A-7B) in that the valve 880 is positioned inside (e.g., disposed within) a housing of the respiratory device 122. As shown, the valve 880 includes an inlet 882, a first outlet 884A, and a second outlet 884B. The valve 880 selectively directs air flow in the same, or similar, manner as the valve 780 (FIGS. 7A-7B) described above. The inlet 882 is coupled to the motor outlet 806. The first outlet 884B of the valve 880 is coupled to a first conduit 810 that delivers at least a portion of the pressurized air from the blower motor 802 to the second outlet 123B. The second outlet 884B of the valve 880 is coupled to a second conduit 820 that delivers at least a portion of the pressurized air from the blower motor 802 to the humidification tank 129. The humidification tank 129 contains a reservoir of water and delivers water vapor to humidify the pressurized air (e.g., such that the pressurized air has a relative humidity between about 30% and about 70%). The pressurized air then exits the humidification tank 129 and is directed to the first outlet 123A via a third conduit 830.

Because the valve 880 is disposed within the respiratory device 122 and is positioned upstream of the blower motor 802, but downstream of the humidification tank 129, at least a portion of the pressurized air from the blower motor 802 can exit the respiratory device 122 through the first outlet 123A without passing through the humidification tank 129. As described herein, the pressurized air directed to the second outlet 123B is eventually directed to the multi-compartment bladder 170 via the second conduit 172. Thus, the positioning of the valve 880 aids in preventing moisture from entering the multi-compartment bladder 170 during inflation, which is undesirable (e.g., the moisture could affect the inflation/deflation of the multi-compartment bladder and/or can cause mold growth or buildup within the multi-compartment bladder).

Referring to FIG. 9, a method 900 for directing at least a portion of the supplied pressurized air from a respirator device to a multi-compartment bladder to adjust a position of a user during a sleep session is illustrated. One or more of the steps of the method 900 can be implemented using the system 100 (FIG. 1) described herein.

Step 901 of the method 900 includes generating or obtaining data (e.g., physiological data) associated with a sleep session of a user. For example, step 901 can include using any combination of the one or more sensors 130 of the system 100 (FIG. 1) to collect data during a sleep session of the user 210 (FIG. 2). In some implementations, the data is generated or obtained using the pressure sensor 132 and/or the flow rate sensor 134 (FIG. 1), which are coupled to or integrated in the respiratory device 122. In other implementations, the data is generated using the microphone 140 and speaker 142, which are coupled to or integrated in the user device 190. Information describing the generated or obtained data can be stored in the memory device 114.

The data described herein can be generated or obtained for the entire sleep session, a portion of the sleep session, or a plurality of portions or segments of the sleep session. In some implementations, the sleep session begins (and data collection starts) when the user 210 enters the bed 230 (FIG. 2) and terminates when the user 210 exits the bed 230. In other implementations, the sleep session begins (and data collection starts) when the user 210 attempts to fall asleep and terminates when the user 210 wakes up. In other implementations, the sleep session begins (and data collection starts) when the user 210 engages the interface 124 (e.g., as shown in FIG. 2) and terminates when the user 210 removes the interface 124.

Step 902 of the method 900 includes analyzing the generated data associated with the sleep session obtained or generated during step 901 using, for example, the processor 112 of the control system 110 of the system 100 (FIG. 1). For example, step 902 can include analyzing the generated data from step 901 to determine a sleep-wake signal for the user during the sleep session. In such implementations, the sleep-wake signal can be indicative of one or more sleep states, including wakefulness, relaxed wakefulness, micro-awakenings, a REM stage, a first non-REM stage, a second non-REM stage, a third non-REM stage, or any combination thereof. The sleep-wake signal can also be indicative of a respiration signal, a respiration rate, an inspiration amplitude, an expiration amplitude, an inspiration-expiration ratio, pressure settings of the respiratory device 122, or any combination thereof. Information describing the sleep-wake signal can be stored in the memory device 114. In some implementations, step 902 also includes analyzing the generated data from the one or more sensors 130 to determine movement data indicative of movement of the user 210 during the sleep session, location data indicative of a location of the user 210 (e.g., a relative location of the head of the user 210) during the sleep session, temperature data indicative of a temperature of the user 210 (e.g., core temperature and/or skin temperature) during the sleep session, an ambient temperature during the sleep session, or any combination thereof.

Step 903 of the method 900 includes determining, based on the data obtained or generated during step 901 and/or the analysis during step 902, that the user is experiencing or has experienced an event. The event can be, for example, snoring, an apnea (e.g., an obstructive apnea, such as positional obstructive sleep apnea), a hypopnea, a restless leg, a sleeping disorder, choking, an increased heart rate, labored breathing, pain (e.g., back pain), an asthma attack, an epileptic episode, a seizure, a mask or interface leak, or any combination thereof. If the user is experiencing or has experienced an event, the method 900 proceeds to step 904. Otherwise, steps 901-903 can be repeated one or more times until an event is detected during 903.

Step 904 of the method 900 includes directing at least a portion of the pressurized air from the respiratory device 122 to the multi-compartment bladder (e.g., the multi-compartment bladder 170, the multi-compartment bladder 370, the multi-compartment bladder 470, or the multi-compartment bladder 570) responsive to determining that the user is experiencing or has experienced an event. The event can be, for example, a positional event (e.g., positional apnea, positional snoring, or a mask or interface leak). As described herein, directing at least a portion of the pressurized air to the multi-compartment bladder modifies (e.g., inflates) the multi-compartment bladder and causes corresponding movement of at least a portion of the user (e.g., the head of the user). Step 904 can include at least partially inflating at least one of the compartments of the multi-compartment bladder, at least partially deflating at least one of the compartments of the multi-compartment bladder, or both, to aid in adjusting a position of the user.

In some implementations, step 904 includes adjusting one or more settings of the respirator device to aid in directing pressurized air to the multi-compartment bladder. For example, prior to step 904, the respirator device may be supplying a volume of pressurized air that is sufficient for delivery to the airway via the interface 124. During step 904, a portion or volume of this pressurized air is directed or diverted to the multi-compartment bladder. Thus, step 904 can include adjusting one or more settings (e.g., pressure, flow rate, etc.) of the respiratory device 122 so that a sufficient volume/pressure of air directed to both the interface 124 and the multi-compartment bladder. Alternatively, in some implementations, the respiratory device 122 is not supplying pressurized air to the user via the interface. In such implementations, step 904 can also include adjusting one or more settings of the respirator device to direct pressurized air to the multi-compartment bladder (e.g., turning on the respirator device).

In some implementations, the respiratory device 122 is not supplying pressurized air to the user via the interface (e.g., the user is not wearing the interface 124, perhaps having discarded the user interface during a sleep session). In such implementations, step 904 can include modifying the multi-compartment bladder to modify the position of the user responsive to identifying a respiratory event (e.g., positional apnea, positional snoring, etc.). Thus, in certain implementations, the user's body position can be changed in order to address or prevent respiratory events, even when the user is not wearing the interface 124 (but the respiratory device 122 is powered on). Step 904 can also include modifying the multi-compartment bladder to adjust the position of the user responsive to determining that the current position of the user is associated with a respiratory event (e.g., based on previously recorded data for the user) to aid in preventing or reducing the likelihood of the user experiencing the event. In other implementations, the system 100 includes the respiratory system 120, and the user is wearing the interface 124, and step 904 can include modifying the multi-compartment bladder to adjust the position of the user responsive to identifying a respiratory event (e.g., positional apnea, positional snoring, etc.) and substantially maintaining or reducing the pressure of the air delivered to the user via the user interface in response to detection of the positional event. Subsequent to the multi-compartment bladder being modified in step 904, steps 901-903 can be repeated to determine if the user is still experiencing the respiratory event, in which case the pressure of the air delivered to the user can be increased to treat the positional event. Further, adjusting the position of the user can advantageously allow use of increased air pressure by, for example, moving the user's head or body to a position more conducive to better mask seal (see, for example, the above discussion in relation to FIGS. 6C and 6D).

In some implementations, step 904 includes determining a location of the user 210 (FIG. 2) relative to the multi-compartment bladder. For example, step 904 can include determining a location of the head of the user 210 (FIG. 1) relative to the multi-compartment bladder using data from one or more of the sensors 130 that is external to the multi-compartment bladder (e.g., the motion sensor 138, the microphone 140 and the speaker 142, the camera 150, infrared sensor 152, and/or the LiDAR sensor 178, or any combination thereof). Alternatively, the location of the head of the user 210 can be determined using or one or more of the sensors 130 (e.g., the capacitive sensor 160, the force sensor 162, and/or the strain gauge sensor 164) that is coupled to or imbedded in the multi-compartment bladder (e.g., as shown in FIGS. 3-4). The control system 110 can determine that the user 210 is positioned on their side (e.g., as shown in FIG. 6C) as opposed to laying on their back (e.g., as shown in FIG. 6D). As another example, using the location data, the control system 110 can determine an angle of the head of the user 210 relative to a horizontal plane (e.g., the mattress and/or the pillow).

In some implementations, step 904 includes determining, based at least in part on the measured pressures from the one or more sensors 130 (FIG. 1), that a first compartment of the multi-compartment bladder is directly supporting at least a portion of the head of the user and a second compartment of the multi-compartment bladder is not directly supporting at least a portion of the head of the user. Responsive to determining that the first compartment is directly supporting the head of the user and that the second compartment is not directly supporting the head of the user, the control system 110 causes at least a portion of the supplied pressurized air from the respiratory device 122 to be directed to the first compartment of the multi-compartment bladder responsive to the determination that the user is experiencing or has experienced the event (step 903). Because the first compartment is directly supporting the head of the user, directing the first volume of the pressurized air to the first compartment can cause corresponding movement of the user. Conversely, because the second compartment is not directly supporting the head, directing pressurized air to the second compartment may not move the head, or may move the head less than the movement caused by inflating the first compartment. In this manner, the volume of the pressurized air can be directed to the compartment(s) of the multi-compartment bladder that are more likely to cause movement of the head of the user.

In some implementations, step 904 includes modifying the multi-compartment bladder according to a predetermined inflation scheme that is associated with the determined event. For example, if the determined event is snoring or choking, which can be caused by a narrowed or closed airway, the multi-compartment bladder can be modified according to a fill scheme that tilts the head of the user 210 forward and/or upward to aid in clearing and/or opening the airway (e.g., inflating the second compartment 374B of the multi-compartment bladder 370 to cause the user 210 to move from a first position (FIG. 6A) to a second position (FIG. 6B) as described herein).

In some implementations, step 904 includes modifying the multi-compartment bladder from an initial fill scheme to a second inflation scheme. In such implementations, the method 900 can include (e.g., prior to step 901) an input indicative of the initial fill scheme. For example, the initial fill scheme can be selected by the user based on comfort to aid the user in falling asleep, selected to position the user to watch TV or read in bed, or more generally customized by the user as desired. Information describing the initial fill scheme can be stored in the memory device 114 (FIG. 1). The multi-compartment bladder is then modified according to second inflation scheme responsive to determining that the user has experienced or is experienced an event (step 903) or in response to determining that the user has fallen asleep (e.g., as determined based on the data from step 901 and analysis during step 902).

In some implementations, subsequent to the multi-compartment bladder being modified in step 904, steps 901-903 are repeated to determine if the user 210 is still experiencing the event. If the user is still experiencing the event, step 904 can be repeated one or more times to continue to modify the multi-compartment bladder as described above until the user is no longer experiencing the event. In such implementations, the inflation scheme coinciding with termination of the ongoing event can be stored in the memory device 114 (FIG. 1) and associated with that event. As such, in the future, the multi-compartment bladder can be inflated according to that fill scheme in step 904 in response to determining that the user 210 is or has experienced the associated event. In other words, the initial inflation scheme can be adjusted based on continued analysis of the data associated with the sleep session.

Alternatively, if the user is still experiencing the event after step 904, in some implementations, the method 900 includes adjusting the settings of the respirator device (e.g., adjusting the air pressure, adjusting the flow rate, adjusting the temperature). For example, the control system 110 can optimally adjust the settings of the respiratory device 122 to match the data (e.g., breathing/respiration pattern) generated or obtained prior to the event. Thus, advantageously, the respirator device settings are only adjusted (e.g., by increasing the air pressure) if repositioning the user 210 via the multi-compartment bladder being modified fails to address the determined event. Alternatively still, in some implementations, the adjustment of the one or more settings of the respirator device can occur simultaneously with the direction of pressurized air from the respiratory device to the multi-compartment bladder (step 904).

Referring to FIG. 10, a method 1000 for adjusting a position of a head of the user during a sleep session is illustrated. One or more steps of the method 1000 can be implemented using the system 100 (FIG. 1) described herein.

Step 1001 of the method 1000 is the same as, or similar to, step 901 of the method 900 (FIG. 9) and includes generating or obtaining data associated with a sleep session of a user. For example, step 1001 includes using any combination of the one or more sensors 130 (FIG. 1) to generate or obtain the data. Step 1002 is the same as, or similar to, step 902 of the method 900 (FIG. 9) and includes analyzing the generated data (step 1001) associated with the sleep session.

Step 1003 of the method 1000 is similar to step 903 of the method 900 (FIG. 9) and includes determining whether the user has experienced or is experiencing a first event or a second event. The first event and the second event are different events. For example, the first event can be, for example, snoring, positional snoring, a positional apnea, a mask or interface leak, or any combination thereof, while the second event can be any of the other events described herein. More generally, the first event is an event associated with the position of the user such that adjusting the position of the user can reduce or eliminate the first event, whereas the second event is not associated with the position of the user such that adjusting the position of the user is not likely to reduce or eliminate the occurrence of the second event. Based on the determination of the first event or the second event in step 1003, the method 1000 proceeds to either step 1004 or step 1005.

Step 1004 of the method 1000 is the same as, or similar to, step 904 of the method 900 (FIG. 9) and includes directing at least a portion of the pressurized air from the respirator device to the multi-compartment bladder to aid in adjusting a position of the user responsive to determining that the user is experiencing the first event.

Step 1005 of the method 1000 includes adjusting pressurized air that is directed to the interface (e.g., the volume delivered to the user and/or flow rate from the respirator device) responsive to determining that the user is experiencing the second event. In some implementations, the respiratory device 122 continuously delivers pressurized air to the user 210 via the first conduit 126 at a first predetermined pressure (e.g., during one or more of steps 1001-1004). In such implementations, responsive to determining that the user is experiencing the second event, the control system 110 causes the valve to increase the volume of pressurized that is directed to the user 210 via the first conduit 126 and/or the flow rate from the respirator device to increase the pressure to a second predetermined pressure that is greater than the first predetermined pressure (e.g., 1.5 times greater, 2 times greater, 5 times greater, 10 times greater, etc.) to treat the second event.

By directing the pressurized air to either the multi-compartment bladder (step 1004) or adjusting the pressurized air delivered to the interface (1005) based on the determined event (step 1003), the method 1000 delivers tailored, efficient therapy to the user. For example, instead of increasing the volume/pressure of the air delivered by the interface 124, which can cause adverse side effects (e.g., sore throat), the method 1000 instead directs pressurized air to the multi-compartment bladder (step 1004) to adjust the position of the user to address the event. On the other hand, the method 1000 directs or diverts air to the interface 124 where the user is experiencing an event that requires an increase in the volume/pressure of the air delivered by the interface 124 and where adjusting the position of the user is not likely to effectively treat or address the event.

While the multi-compartment bladders have been described herein as being used to adjust a position of a user responsive to determining that the user is experiencing or has experienced a sleep-related event, the same, or similar, multi-compartment bladders can be used to aid in preventing or reducing the likelihood of infant flat-head syndrome by adjusting a position of the infant (e.g., the head of the infant). The multi-compartment bladders described herein can also be used to adjust a position of a user that is confined to a bed to prevent and/or reduce the likelihood of the user developing bed sores, back pain, etc. Furthermore, the multi-compartment bladders described herein can be used to balance the need to treat or prevent events, such as (positional) apnea events, mask leaks, etc., with the need to reduce or avoid development of bed sores, back pain, etc. For example, when no events are detected or predicted, the multi-compartment bladder can periodically adjust the position of a user to reduce or avoid development of bed sores, back pain, etc. In other examples, when no bed sores, back pain, etc. are detected or reported, the multi-compartment bladder can adjust the position of a user to treat or prevent events at a frequency and duration as required.

In some implementations, respiratory events can be monitored (e.g., snoring events monitored by an acoustic sensor) relative to the user's position and/or the inflation status of the multi-compartment bladder. Such monitoring can be to learn, for example, via a machine learning model, the user position(s) and/or the inflation status which results is reduced number of events, reduced number of arousals, optimized sleep patterns, or any combination thereof. Similarly, in some implementations, the actuation and inflation status of the multi-compartment bladder 14 can be monitored, along with the user's sleep state (such as wakefulness, relaxed wakefulness, micro-awakenings, a rapid eye movement (REM) stage, a first non-REM stage (N1), a second non-REM stage (N2), a third non-REM stage (N3), determined by, for example, a sleep-wake signal as described herein), to learn how the actuation and inflation status of the multi-compartment bladder affects the user's sleep in terms of sleep cycles, wake times, etc., and thereby how to minimize the effects on the user's sleep caused by the multi-compartment bladder. For example, if actuation of the multi-compartment bladder early in a sleep session, and/or in a particular sleep state, results in awakenings, then actuation of the multi-compartment bladder during those times is minimized or avoided for that user.

Figure 11:
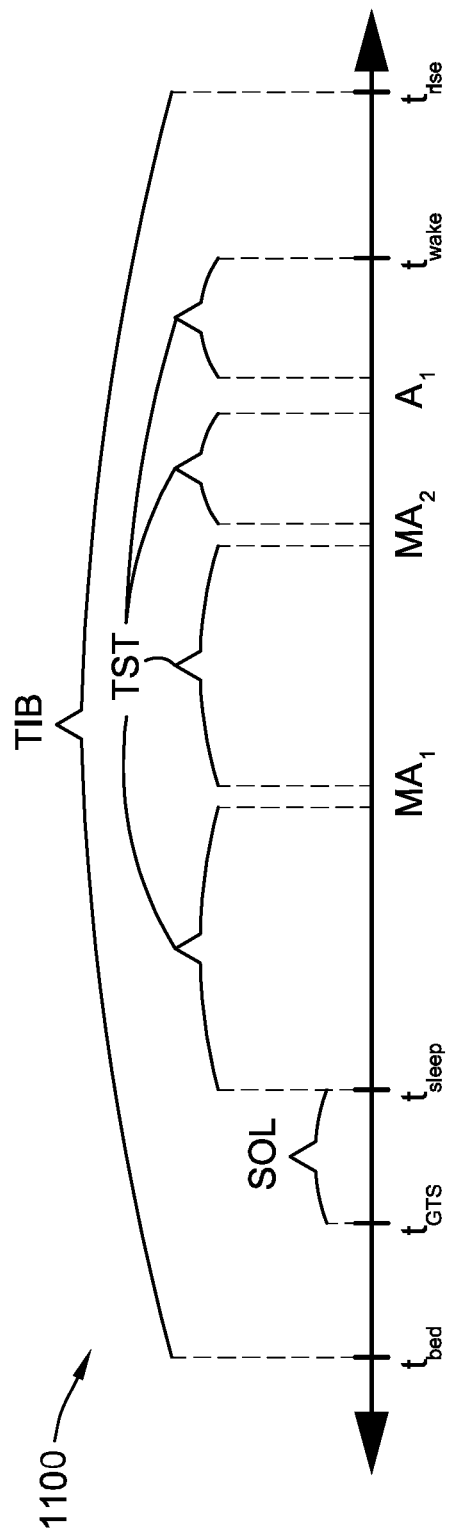
FIG. 11 illustrates an exemplary timeline for a sleep session, according to some implementations of the present disclosure.

As used herein, a sleep session can be defined in a number of ways based on, for example, an initial start time and an end time. Referring to FIG. 11, an exemplary timeline 1100 for a sleep session is illustrated. The timeline 1100 includes an enter bed time ($t_{bed}$), a go-to-sleep time ($t_{GTS}$), an initial sleep time ($t_{sleep}$), a first micro-awakening $MA_1$ and a second micro-awakening $MA_2$, a wake-up time ($t_{wake}$), and a rising time ($t_{rise}$).

As used herein, a sleep session can be defined in multiple ways. For example, a sleep session can be defined by an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) one or more user-selectable element that is displayed on the display 192 of the user device 190 (FIG. 1) to manually initiate or terminate the sleep session.

Referring to the timeline 1100 in FIG. 11, the enter bed time $t_{bed}$ is associated with the time that the user initially enters the bed (e.g., bed 230 in FIG. 2) prior to falling asleep (e.g., when the user lies down or sits in the bed). The enter bed time $t_{bed}$ can be identified based on a bed threshold duration to distinguish between times when the user enters the bed for sleep and when the user enters the bed for other reasons (e.g., to watch TV). For example, the bed threshold duration can be at least about 10 minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time $t_{bed}$ can refer to the time the user initially enters any location for sleeping (e.g., a couch, a chair, a sleeping bag, etc.).

The go-to-sleep time (GTS) is associated with the time that the user initially attempts to fall asleep after entering the bed ($t_{bed}$). For example, after entering the bed, the user may engage in one or more activities to wind down prior to trying to sleep (e.g., reading, watching TV, listening to music, using the user device 190, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings $MA_1$ and $MA_2$) having a short duration (e.g., 5 seconds, 10 seconds, 30 seconds, 1 minute, etc.) after initially falling asleep. In contrast to the wake-up time $t_{wake}$, the user goes back to sleep after each of the microawakenings $MA_1$ and $MA_2$. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based on a wake threshold duration (e.g., the user is awake for at least 15 minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based on a rise threshold duration (e.g., the user has left the bed for at least 15 minutes, at least 20 minutes, at least 30 minutes, at least 1 hour, etc.). The enter bed time $t_{bed}$ time for a second, subsequent sleep session can also be defined based on a rise threshold duration (e.g., the user has left the bed for at least 4 hours, at least 6 hours, at least 8 hours, at least 12 hours, etc.).

As described above, the user may wake up and get out of bed one more times during the night between the initial $t_{bed}$ and the final $t_{rise}$. In some implementations, the final wake-up time $t_{wake}$ and/or the final rising time $t_{rise}$ that are identified or determined based on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed ($t_{bed}$), going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based on the system monitoring the user's sleep behavior.

The total time in bed (TIB) is the duration of time between the time enter bed time $t_{bed}$ and the rising time $t_{rise}$. The total sleep time (TST) is associated with the duration between the initial sleep time and the wake-up time, excluding any conscious or unconscious awakenings and/or micro-awakenings therebetween. Generally, the total sleep time (TST) will be shorter than the total time in bed (TIB) (e.g., one minute short, ten minutes shorter, one hour shorter, etc.). For example, referring to the timeline 300 of FIG. 3, the total sleep time (TST) spans between the initial sleep time $t_{sleep}$ and the wake-up time $t_{wake}$, but excludes the duration of the first micro-awakening $MA_1$, the second micro-awakening $MA_2$, and the awakening A. As shown, in this example, the total sleep time (TST) is shorter than the total time in bed (TIB).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time ($t_{bed}$) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time ($t_{bed}$) and ending at the wake-up time ($t_{wake}$). In some implementations, a sleep session is defined as starting at the initial sleep time ($t_{sleep}$) and ending at the rising time ($t_{rise}$).

Figure 12:
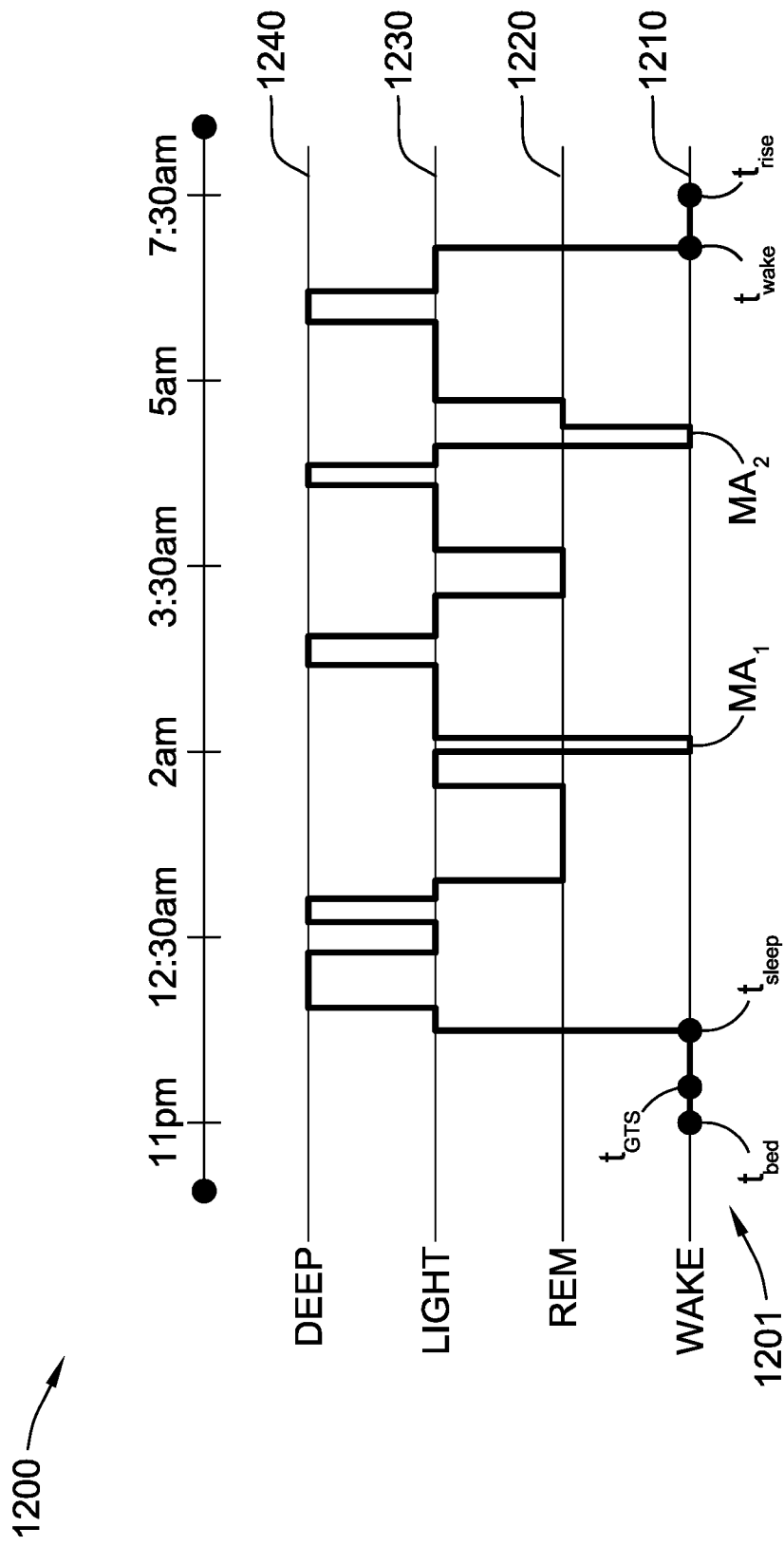
FIG. 12 illustrates an exemplary hypnogram associated with the sleep session of FIG. 11, according to some implementations of the present disclosure.

Referring to FIG. 12, an exemplary hypnogram 1200 corresponding to the timeline 1100 (FIG. 11), according to some implementations, is illustrated. As shown, the hypnogram 1200 includes a sleep-wake signal 1201, a wakefulness stage axis 1210, a REM stage axis 1220, a light sleep stage axis 1230, and a deep sleep stage axis 1240. The intersection between the sleep-wake signal 1201 and one of the axes 1210-1240 is indicative of the sleep stage at any given time during the sleep session.

The sleep-wake signal 1201 can be generated based on physiological data associated with the user (e.g., generated by one or more of the sensors 130 described herein). The sleep-wake signal can be indicative of one or more sleep states, including wakefulness, relaxed wakefulness, microawakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 1200 is shown in FIG. 12 as including the light sleep stage axis 1230 and the deep sleep stage axis 1240, in some implementations, the hypnogram 1200 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration ratio, a number of events per hour, a pattern of events, or any combination thereof. Information describing the sleep-wake signal can be stored in the memory device 114.

The hypnogram 1200 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 12), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 12), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

In some implementations, the systems and methods described herein can include generating or analyzing a hypnogram including a sleep-wake signal to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof based at least in part on the sleep-wake signal of a hypnogram.

In other implementations, one or more of the sensors 130 can be used to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time $t_{bed}$ can be determined based on, for example, data generated by the motion sensor 138, the microphone 140, the camera 150, or any combination thereof. The go-to-sleep time can be determined based on, for example, data from the motion sensor 138 (e.g., data indicative of no movement by the user), data from the camera 150 (e.g., data indicative of no movement by the user and/or that the user has turned off the lights) data from the microphone 140 (e.g., data indicative of the using turning off a TV), data from the user device 190 (e.g., data indicative of the user no longer using the user device 190), data from the pressure sensor 132 and/or the flow rate sensor 134 (e.g., data indicative of the user turning on the respiratory device 122, data indicative of the user donning the user interface 124, etc.), or any combination thereof.

One or more elements or aspects or steps, or any portion(s) thereof, from one or more of any of the claims below can be combined with one or more elements or aspects or steps, or any portion(s) thereof, from one or more of any of the other claims or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A system comprising:
a respiratory device configured to supply, by way of a user interface coupled to the respiratory device via a conduit, pressurized air to an airway of a user during a sleep session;
a sensor configured to generate data associated with the sleep session;
a multi-compartment bladder coupled to the respiratory device and being configured to be positioned adjacent to the user during the sleep session;
a memory storing machine-readable instructions; and
a control system including one or more processors configured to execute the machine-readable instructions to:
determine, based at least in part on the data, that the user is experiencing or has experienced an event; and
cause at least a portion of the supplied pressurized air to be directed to the multi-compartment bladder responsive to determining that the user is experiencing or has experienced the event.

2. The system of claim 1, further comprising a valve, the valve being configured to direct the supplied pressurized air to the interface, the multi-compartment bladder, or both.

3. The system of claim 2, wherein the valve is configured to direct the supplied pressurized air to the interface and the multi-compartment bladder at the same time.

4. The system of claim 3, wherein responsive to the determination that the user is experiencing or has experienced the event, the control system is further configured to execute the machine-readable instructions to cause the respirator device to (i) increase a pressure of the supplied pressurized air, (ii) increase a flow rate of the supplied pressurized air, (iii) or both.

5. The system of claim 2, wherein the valve is configured to direct the supplied pressurized air to the user interface and the multi-compartment bladder in an alternating fashion.

6. The system of claim 1, further comprising one or more pressure sensors configured to measure a pressure within one or more compartments of the multi-compartment bladder, and wherein the control system is further configured to determine, based at least in part on the measured pressure, a location of a head of the user relative to the multi-compartment bladder and determine, based at least in part on the measured pressures, that a first compartment of the multi-compartment bladder is directly supporting at least a portion of the head of the user and a second compartment of the multi-compartment bladder is not directly supporting at least a portion of the head of the user.

7. The system of claim 1, further comprising an external device that is separate and distinct from the respiratory device, the external device including one or more sensors and the control system is further configured to determine, based at least in part on an output from the one or more sensors of the external device, a location of a head of the user relative to the multi-compartment bladder.

8. The system of claim 1, wherein the multi-compartment bladder includes an exit valve, the exit valve being configured to be activated to permit the supplied pressurized air within the multi-compartment bladder to escape.

9. The system of claim 1, wherein the event includes snoring, an apnea, a hypopnea, an interface leak, a restless leg, a sleeping disorder, choking, an increased heart rate, labored breathing, an asthma attack, an epileptic episode, a seizure, or any combination thereof.

10. The system of claim 1, wherein the multi-compartment bladder has a generally U-shape.

11. The system of claim 10, wherein the multi-compartment bladder includes at least three separate and distinct compartments.

12. The system of claim 11, wherein the at least three separate and distinct compartments are fluidly coupled in series.

13. The system of claim 11, wherein the at least three separate and distinct compartments are independent and configured to be inflated independently from one another.

14. The system of claim 1, wherein causing the at least a portion of the supplied pressurized air to be directed to the multi-compartment bladder causes the multi-compartment bladder to be modified according to a first inflation scheme.

15. The system of claim 14, wherein the control system is further configured to, (i) subsequent to the multi-compartment bladder being modified according to the first inflation scheme, continue to analyze the data to determine if the user is still experiencing the event and (ii) responsive to the continued analysis of the generated data resulting in a determination that the user is still experiencing the event, cause the multi-compartment bladder to be modified according to a second inflation scheme.

16. A system comprising:
a respiratory device configured to supply, by way of a user interface coupled to the respiratory device via a first tube, pressurized air to an airway of a user during a sleep session;
a sensor configured to generate data associated with the sleep session;
a multi-compartment bladder coupled to the respiratory device via a second tube;
a valve in fluid communication with the respiratory device, the first tube, and the second tube;
a memory storing machine-readable instructions; and
a control system including one or more processors configured to execute the machine-readable instructions to:
determine that the user is experiencing or has experienced an event based at least in part on the data; and
responsive to determining that the user is experiencing or has experienced the event, cause the valve to direct at least a portion of the supplied pressurized air to the multi-compartment bladder via the second tube to aid in causing a head of the user to move.

17. The system of claim 16, wherein the supplied pressurized air delivered to the multi-compartment bladder causes the head of the user to move about a longitudinal axis from a first position towards a second position.

18. The system of claim 17, wherein the event includes an interface leak and moving from the first position towards the second position aids in the increasing the engagement between the user interface and the user.

19. The system of claim 16, wherein the supplied pressurized air delivered to the multi-compartment bladder causes the head of the user to move about a transverse axis from a first position to a second position.

20. The system of claim 16, wherein the event includes snoring, an apnea, a hypopnea, an interface leak, a restless leg, a sleeping disorder, choking, an increased heart rate, labored breathing, an asthma attack, an epileptic episode, a seizure, or any combination thereof.

21. The system of claim 16, wherein the valve is configured to deliver a first portion the supplied pressurized air to the first tube and simultaneously deliver a second portion of the supplied pressurized air to the second tube.

22. The system of claim 21, wherein the first portion of the supplied pressurized air has a first pressure and the second portion of the supplied pressurized air has a second pressure that is different than the first pressure.

23. The system of claim 22, wherein the first pressure is between about 0.2 PSI and about 0.25 PSI.

24. The system of claim 16, wherein the respiratory device has a first outlet and a second outlet, the first tube being coupled to and in fluid communication with the first outlet, the second tube being coupled to and in fluid communication with the second outlet, wherein the valve causes a first portion of the pressurized air to be delivered to the first outlet and a second portion of the pressurized air to the second outlet.

25. A system comprising:
- a respiratory device configured to supply, by way of a user interface coupled to the respiratory device via a conduit, pressurized air to an airway of the user during a sleep session;
- a sensor configured to generate data associated with the sleep session of the user;
- a multi-compartment bladder coupled to the respiratory device and being configured to be positioned adjacent to the user during the sleep session;
- a memory storing machine-readable instructions; and
- a control system including one or more processors configured to execute the machine-readable instructions to:
  - determine, based at least in part on the data, that the user is experiencing or has experienced a first event or a second event,
  - responsive to determining that the user is experiencing or has experienced the first event, cause (i) a first portion of the supplied pressurized air from the respiratory device to be directed to the multi-compartment bladder to aid in causing the user to move and (ii) a second portion of the supplied pressurized air from the respiratory device to be directed to the user interface, and
  - responsive to determining that the user is experiencing or has experienced the second event, cause the supplied pressurized air from the respiratory device to be directed to the user interface.

26. The system of claim 25, wherein the first portion of the supplied pressurized air delivered to the multi-compartment bladder has a first pressure and the second portion of the supplied pressurized air delivered to the user interface has a second pressure that is different than the first pressure.

27. The system of claim 26, wherein the supplied pressurized air delivered to the user interface responsive to the determination that the user is experiencing or has experienced the second event has a third pressure that is greater than the second pressure.

* * * * *